(12) United States Patent
Kirsch et al.

(10) Patent No.: US 10,364,356 B2
(45) Date of Patent: Jul. 30, 2019

(54) DEVICE FOR REGULATING THE PASSAGE OF ENERGY

(71) Applicant: Merck Patent GmbH, Darmstadt (DE)

(72) Inventors: Peer Kirsch, Seeheim-Jugenheim (DE); Susann Gunst, Darmstadt (DE); Michael Junge, Pfungstadt (DE); Andreas Beyer, Hanau (DE); Ursula Patwal, Reinheim (DE)

(73) Assignee: Merck Patent GmbH, Darmstadt (DE)

( * ) Notice: Subject to any disclaimer, the term of this patent is extended or adjusted under 35 U.S.C. 154(b) by 167 days.

(21) Appl. No.: 15/534,009

(22) PCT Filed: Nov. 11, 2015

(86) PCT No.: PCT/EP2015/002261
§ 371 (c)(1),
(2) Date: Jun. 8, 2017

(87) PCT Pub. No.: WO2016/091345
PCT Pub. Date: Jun. 16, 2016

(65) Prior Publication Data
US 2018/0335654 A1    Nov. 22, 2018

(30) Foreign Application Priority Data

Dec. 9, 2014    (EP) .................................... 14004145

(51) Int. Cl.
*C09B 57/00* (2006.01)
*C07D 513/04* (2006.01)
(Continued)

(52) U.S. Cl.
CPC ............ *C09B 57/00* (2013.01); *C07D 513/04* (2013.01); *C07D 517/04* (2013.01);
(Continued)

(58) Field of Classification Search
None
See application file for complete search history.

(56) References Cited

U.S. PATENT DOCUMENTS 10,108,058 B2    10/2018  Junge et al.
2006/0052612 A1*  3/2006  Stossel ................ C07D 285/14
                                                  548/126

(Continued)

FOREIGN PATENT DOCUMENTS

WO    2013/005177 A2    1/2013
WO      13005177 A2    1/2013
(Continued)

OTHER PUBLICATIONS

International Search Report dated Mar. 3, 2016 issued in corresponding PCT/EP2015/002261 application (2 pages).
(Continued)

*Primary Examiner* — Cynthia H Kelly
*Assistant Examiner* — Anna Malloy
(74) *Attorney, Agent, or Firm* — Millen White Zelano and Branigan, PC

(57) ABSTRACT

The present application relates to novel compounds and to devices which contain these compounds. The application also relates to a device for regulating the passage of energy from an outside space into an inside space, to a window containing the said device, and to uses of the said devices and compounds.

15 Claims, 1 Drawing Sheet

(51) Int. Cl.
| | |
|---|---|
| C07D 517/04 | (2006.01) |
| C09K 19/34 | (2006.01) |
| C09K 19/60 | (2006.01) |
| F24S 20/63 | (2018.01) |
| F24S 50/80 | (2018.01) |
| G02F 1/13 | (2006.01) |
| G02F 1/137 | (2006.01) |
| H01L 31/055 | (2014.01) |

(52) U.S. Cl.
CPC .......... *C09K 19/3497* (2013.01); *C09K 19/60* (2013.01); *F24S 20/63* (2018.05); *F24S 50/80* (2018.05); *G02F 1/132* (2013.01); *G02F 1/137* (2013.01); *H01L 31/055* (2013.01); *C09K 2219/13* (2013.01); *G02F 2001/13712* (2013.01); *G02F 2202/043* (2013.01); *G02F 2202/046* (2013.01); *Y02B 10/20* (2013.01)

(56) References Cited

U.S. PATENT DOCUMENTS

| | | | |
|---|---|---|---|
| 2008/0204644 A1* | 8/2008 | Toyama | G02F 1/133634 349/118 |
| 2010/0210762 A1* | 8/2010 | Hanaki | A61K 8/49 524/83 |
| 2014/0303379 A1 | 10/2014 | Santarelli et al. | |
| 2015/0059853 A1* | 3/2015 | Tokito | C07D 513/04 136/263 |
| 2016/0085108 A1 | 3/2016 | Junge et al. | |
| 2016/0108317 A1 | 4/2016 | Kirsch et al. | |

FOREIGN PATENT DOCUMENTS

| | | | |
|---|---|---|---|
| WO | WO-2013005177 A2 * | 1/2013 | ............ C09B 57/00 |
| WO | 2014/132978 A1 | 9/2014 | |
| WO | 14132978 A1 | 9/2014 | |
| WO | 2014/180525 A1 | 11/2014 | |
| WO | 2014/187529 A1 | 11/2014 | |
| WO | 14180525 A1 | 11/2014 | |
| WO | 14187529 A1 | 11/2014 | |

OTHER PUBLICATIONS

W. R. Hatchard, "The Synthesis of Isothiazoles. I. 3,5-Dichloro-4-isothiazolecarbonitrile and Its Derivatives", Journal of Organic Chemistry, 1964, 29, pp. 660-665.

Li et al., "5,6-Difluorobenzothiadiazole and silafluorene based conjugated polymers for organic photovoltaic cells", Journal of Materials Chemistry C, 2014, 2, pp. 5116-5123.

Schroeder et al., "Silaindacenodithiophene-Based Low Band Gap Polymers—The Effect of Fluorine Substitution on Device Performances and Film Morphologies". Advanced Functional Materials, 2012, 22, pp. 1663-1670.

Zhang et al., "Benzo-2,1,3-thiadiazole-based, highly dichroic fluorescent dyes for fluorescent host-guest liquid crystal displays", Journal of Materials Chemistry, 2004, 14, pp. 1901-1904.

Zhang et al., "Increased open circuit voltage in fluorinated benzothiadiazole-based alternating conjugated polymers", Chemical Communication, 2011, 47, pp. 11026-11028.

* cited by examiner

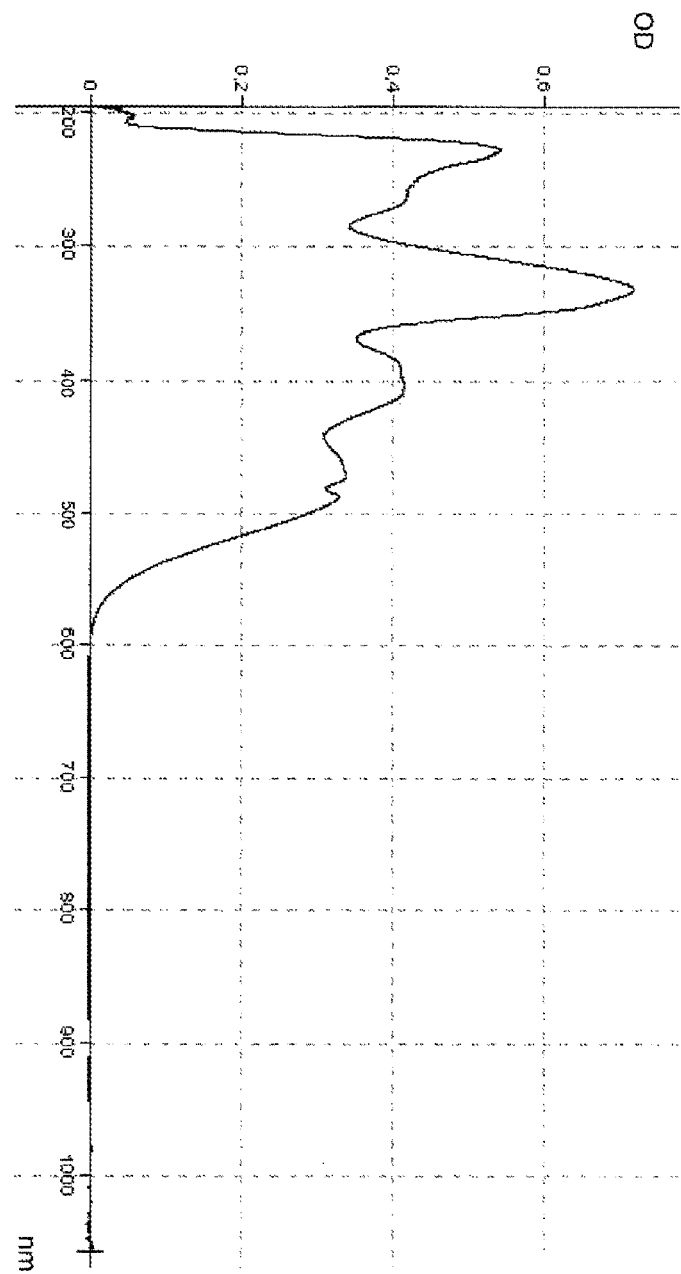

DEVICE FOR REGULATING THE PASSAGE OF ENERGY

The present application relates to compounds and devices for regulating the passage of energy from an outside space into an inside space, to specific devices, such as windows, and to uses of the compounds and devices.

A device for regulating the passage of energy is in the present application generally taken to mean a device which regulates the passage of energy through an area which has relatively high energy transmissivity. This area of relatively high energy transmissivity is preferably arranged within a structure of relatively lower energy transmissivity. For example, the area of high energy transmissivity can be a glass area or an open area, and the structure of lower energy transmissivity which contains the area of high energy transmissivity can be a wall.

The device preferably regulates the passage of energy from insolation, either directly or indirectly.

The regulated passage of energy takes place from an outside space, preferably the environment exposed directly to insolation, into an inside space, for example a building or a vehicle, or another unit which is substantially sealed off from the environment.

For the purposes of the present invention, the term energy is taken to mean, in particular, energy by electromagnetic radiation in the UV-A, VIS and NIR region. In particular, it is taken to mean energy by radiation which is not absorbed or is only absorbed to a negligible extent by the materials usually used in windows (for example glass). According to the definitions usually used, the UV-A region is taken to mean a wavelength of 320 to 380 nm, the VIS region is taken to mean a wavelength of 380 nm to 780 nm and the NIR region is taken to mean a wavelength of 780 nm to 2000 nm. Correspondingly, the term light is generally taken to mean electromagnetic radiation having wavelengths between 320 and 2000 nm.

In the area of devices for regulating the passage of energy from an outside space into an inside space, a number of different technical solutions have been proposed in past years.

An advantageous solution is the use of switching layers comprising a liquid-crystalline medium in combination with one or more dichroic dyes. By application of a voltage, a change in the spatial alignment of the molecules of the dichroic compound can be achieved in these switching layers, causing a change in their absorption and thus the transmission through the switching layer. A corresponding device is described, for example, in WO 2009/141295.

For the purposes of the present application, a dichroic dye is taken to mean a light-absorbing compound in which the absorption properties are dependent on the orientation of the compound to the polarisation direction of the light. A dichroic dye compound typically has an elongated shape, i.e. the compound is significantly longer in one spatial direction (longitudinal direction) than in the other two spatial directions.

Alternatively, a change in transmission of this type can also be achieved without electrical voltage by a temperature-induced transition from an isotropic state of the liquid-crystalline medium to a liquid-crystalline state, as described, for example, in US 2010/0259698.

It is furthermore known to design devices having a switching layer comprising a liquid-crystalline medium comprising at least one dichroic dye in such a way that the energy absorbed by the dye is partly re-emitted as fluorescence radiation, which is itself conducted to a solar cell, which converts it into electrical energy (WO 2009/141295).

It is of particular interest to employ fluorescent dyes, which are known for their high light fastness, for the said purposes. These include perylene and terrylene derivatives, but their stability is in need of improvement in that case of extreme requirements for use in windows. Although benzothiadiazole and diketopyrrolopyrrole derivatives meet the requirements with respect to light fastness and dichroism, they often absorb, however, at excessively short wavelengths, meaning that the blue-green colour region can only be covered to an inadequate extent (Zhang et al., 2004, 14; WO2004/090046).

Li et al, 2014, describe derivatives of difluorobenzothiadiazoles and uses in organic photovoltaic cells.

In the case of the known devices for regulating the passage of energy, there is great interest in the development of improved devices and compounds which are suitable for this purpose.

The invention is therefore based on the object of providing novel, improved compounds and devices for regulating the passage of energy from an outside space into an inside space which overcome the disadvantages described above. It should be possible here to use the compounds, in particular, in a switching layer.

The invention is based, in particular, on the object of providing novel dyes having strong fluorescence, high light fastness, a high dichroic ratio and good solubility in typical liquid-crystal mixtures. The compounds should meet the particular demands made in applications in connection with windows, in particular in active, liquid crystal-based shading devices.

The compounds should have strong light absorption in the VIS and/or NIR region of light. The invention is based, in particular, on the object of providing compounds which exhibit good absorption above 450 nm. In particular, the should have a small band gap and an absorption band >450 nm. For compounds and devices which convert emitted fluorescent light into electrical energy, it is furthermore of interest that the compounds have a high fluorescence quantum yield, high relative fluorescence from wave conduction and a high Stokes shift. The compounds should also have a high degree of order in liquid-crystalline mixtures.

The compounds and devices should also have a long lifetime and a large switching range (i.e. the difference in transmission in the bright state to the dark state). Furthermore, there is potential for improvement with respect to the energy yield in the case of devices which utilise the fluorescence emission of the dyes for the recovery of energy by means of a solar cell. In the optimum case, the energy provided by the solar cell should be sufficient in order to provide all the energy necessary for operation of the device, or even exceed this amount.

The compounds should also be suitable for other applications, for example organic solar cells, liquid-crystal displays and organic electronic components, such as semiconductors, diodes or OLEDs.

Surprisingly, it has now been found that the said technical objects are achieved by compounds and devices in accordance with the patent claims.

The invention relates to compounds of the formula (I):

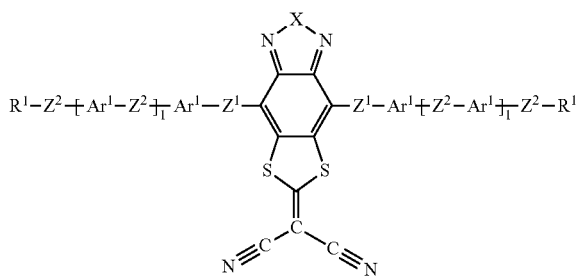

formula (I)

where:
X is equal to S or Se;
$Z^1$ is, independently of one another, a single bond, —$CR^3$=$CR^3$— or —C≡C—; or two, three, four or five groups combined with one another, selected from the groups —$CR^3$=$CR^3$— and —C≡C—;
$Z^2$ is, independently of one another, a single bond, O, S, $C(R^3)_2$, —$CR^3$=$CR^3$— or —C≡C—; or two, three, four or five groups combined with one another, selected from the groups O, S, $C(R^3)_2$, —$CR^3$=$CR^3$— and —C≡C—;
$Ar^1$ is, independently of one another, an aryl or heteroaryl group having 5 to 30 aromatic ring atoms, which may be substituted by one or more radicals $R^4$;
$R^1$ is, independently of one another, H, D, F, CN, $N(R^5)_2$, or an alkyl, alkoxy or thioalkoxy group having 1 to 20 C atoms, which may be substituted by one or more radicals $R^5$, where one or more $CH_2$ groups in the alkyl, alkoxy or thioalkoxy groups may be replaced by —$R^5$C=$CR^5$—, —C≡C—, C=O, C=S, —C(=O) O—, —OC(=O)—, $Si(R^5)_2$, $NR^5$, —O— or —S—;
$R^3$, $R^4$ are, independently of one another, H, D, F, Cl, CN, or an alkyl, alkoxy or thioalkoxy group having 1 to 10 C atoms, which may be substituted by one or more radicals $R^5$, where one or more $CH_2$ groups in the alkyl, alkoxy or thioalkoxy groups may be replaced by —$R^5$C=$CR^5$—, —C≡C—, C=O, C=S, —C(=O) O—, —OC(=O)—, $Si(R^5)_2$, $NR^5$, —O— or —S—;
$R^5$ is, independently of one another, H, D, F, Cl, CN, $N(R^6)_2$, an alkyl, alkoxy or thioalkoxy group having 1 to 10 C atoms or an alkenyl or alkynyl group having 2 to 20 C atoms, where the above-mentioned groups may each be substituted by one or more radicals $R^6$ and where one or more $CH_2$ groups in the above-mentioned groups may be replaced by —$R^6$C=$CR^6$—, —C≡C—, C=O, C=S, —C(=O)O—, —O(C=O)—, $Si(R^6)_2$, $NR^6$, —O— or —S—, or an aryl or heteroaryl group having 5 to 30 aromatic ring atoms, which may in each case be substituted by one or more radicals $R^6$;
$R^6$ is, independently of one another, H, F or an aliphatic organic radical having 1 to 20 C atoms, in which one or more H atoms may be replaced by F, or an aryl or heteroaryl group having 5 to 20 C atoms, in which one or more H atoms may be replaced by F;
i is, independently of one another, equal to 0, 1, 2, 3, 4 or 5.

If i is greater than 1, the groups within the brackets may be identical or different.

If i is equal to 0, the group within the brackets is absent, and the groups $Ar^1$ and $Z^2$ are connected directly to one another.

The compound of the formula (I) is a dye. This means that it at least partially absorbs light in the visible region. The compound is preferably dichroic. This means that it absorbs light to different extents depending on the polarisation. The compound is, in particular, a dichroic dye.

The compounds of the formula (I) contain a central sub-unit 2-(2,5,7-trithia-1,3-diaza-s-indacen-6-ylidene)malononitrile (TDIM), which is depicted between the two radicals $Z^1$ in formula (I). This structural unit has three fused rings, which form a heterocyclic derivative of indacene. The sulfur atom at the C2 position can be replaced here, as depicted in formula (I), by selenium.

The formulation "two, three, four or five groups combined with one another, selected from the groups . . . " in the sense of the present application is taken to mean that the groups are bonded to one another, preferably in the form of a chain in which two, three, four or five of the groups are bonded to one another. Preference is given to a combination of precisely two or three groups. The groups can generally be identical or different.

The compounds of the formula (I) have advantages over the prior art and thus achieve the object on which the invention is based. The compounds exhibit extreme light fastness, for example compared with perylenediimide derivatives, in solution in a liquid-crystalline host. In addition, they exhibit long-wave absorption, and high dichroism in combination with very good solubility. A particular advantage is also the possibility of adjusting the absorption and emission maxima to their respective requirements by variation of the electron-donor properties of the side chains. The compounds also have a high degree of order in liquid-crystalline mixtures, which is generally higher than that of benzothiadiazole derivatives.

An essential advantage is the position of the fluorescence emission maximum beyond the sensitivity range of the human eye. In applications such as, for example, switchable windows based on liquid-crystalline guest-host systems, this enables utilisation of the emitted radiation for the electricity supply of energy self-sufficient systems with the aid of solar cells without the fluorescence light, which is invisible to the eye, resulting in irritating interfering effects in such window systems.

The compound of the formula (I) preferably has two or three aromatic groups on each side of the central unit. The aromatic groups of the compound of formula (I) preferably form a chain.

In the formula (I), the groups shown can generally be identical to or different from one another. Thus, if a compound of the formula (I) contains two or more groups which are denoted by identical placeholders in the formula, such as, for example, $Ar^1$, the two or more groups $Ar^1$ may be identical to or different from one another.

An aryl group in the sense of this invention contains 6 to 30 aromatic ring atoms; a heteroaryl group in the sense of this invention contains 5 to 30 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated)

aromatic or heteroaromatic polycycle in the sense of the present application consists of two or more simple aromatic or heteroaromatic rings condensed with one another. A polycycle of this type may also contain individual non-conjugated units, as in the case, for example, of the fluorene basic structure.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, fluorene, spirobifluorene, furan, benzofuran, isobenzofuran, dibenzofuran, thiophene, benzothiophene, isobenzothiophene, dibenzothiophene, benzodithiophene, cyclopentadithiophene, thienothiophene, indenothiophene, dithienopyrrole, silolodithiophene, selenophene, benzoselenophene, dibenzoselenophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole. The heteroaryl groups of the compound (I) are preferably different from the central TDIM group.

For the purposes of the present invention, an alkyl group having 1 to 10 C atoms or an alkenyl or alkynyl group having 2 to 10 C atoms, in which, in addition, individual H atoms or $CH_2$ groups may be substituted by the groups mentioned under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl.

An alkoxy or thioalkoxy group having 1 to 10 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

An aliphatic organic radical having 1 to 20 C atoms is in principle taken to mean any desired organic radical which is not aromatic or heteroaromatic. It is preferably taken to mean alkyl groups having 3 to 20 or 4 to 15 C atoms, alkoxy groups having 3 to 20 or 4 to 15 C atoms or alkenyl or alkynyl groups having 2 to 10 C atoms, as described in greater detail above.

X preferably stands for S. The central group in formula (I) is then a TDIM structural unit. For the purposes of this application, the term TDIM is used as abbreviation for 2-(2,5,7-trithia-1,3-diaza-s-indacen-6-ylidene)malononitrile, as shown in formula (I).

The sulfur atom at the C2 position may be replaced by selenium in all compounds described below, as depicted in formula (I) by means of the substituent X. This is preferably not the case.

$Z^1$ preferably stands on each occurrence, identically or differently, for a single bond, $-CR^3=CR^3-$ or $-C\equiv C-$. $Z^1$ is particularly preferably a single bond.

$Z^2$ preferably stands on each occurrence, identically or differently, for a single bond, $-C(R^3)_2C(R^3)_2-$, $-CR^3=CR^3-$, $-C\equiv C-$, $-OC(R^3)_2-$ or $-C(R^3)_2O-$, particularly preferably for a single bond, $-CH_2CH_2-$, $-CF_2CF_2-$, $-CH=CH-$, $-CF=CF-$, $-C\equiv C-$, $-OCH_2-$, $-OCF_2-$, $-CH_2O-$ or $-CF_2O-$. $Z^2$ is particularly preferably a single bond.

$Ar^1$ preferably represents on each occurrence, identically or differently, an aryl group having 6 to 15 C atoms or a heteroaryl group having 5 to 15 C atoms, which may be substituted by one or more radicals $R^4$. $Ar^1$ is particularly preferably selected on each occurrence, identically or differently, from benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopentadithiophene, thienothiophene, indenothiophene, dithienopyrrole, silolodithiophene, selenophene, benzoselenophene, dibenzoselenophene, furan, benzofuran, dibenzofuran and quinoline, each of which is optionally substituted by radicals $R^4$. Particular preference is given to benzene or thiophene, each of which may optionally be substituted by fluorine, preferably one or two fluorine per ring.

The group $R^1$ is preferably on each occurrence, identically or differently, H, F, CN, $N(R^5)_2$, or a straight-chain alkyl or alkoxy group having 1 to 20 C atoms, which may be substituted by one or more radicals $R^5$, or a branched alkyl or alkoxy group having 3 to 20 C atoms, which may be substituted by one or more radicals $R^5$, or a cyclic alkyl group having 4 to 8 C atoms, which may be substituted by one or more radicals $R^5$, where one or more $CH_2$ groups in the alkyl and alkoxy groups may be replaced by $-O-$, $-S-$ or $-R^5C=CR^5-$, or a siloxanyl group having 1 to 10 Si atoms, which may be substituted by one or more radicals $R^5$.

$R^1$ is particularly preferably selected, independently of one another, from H, F, or a straight-chain alkyl or alkoxy group having 3 to 20 C atoms, which may be substituted by one or more radicals $R^5$, or a branched alkyl or alkoxy group having 3 to 20 C atoms, which may be substituted by one or more radicals $R^5$, or a cyclic alkyl group having 6 C atoms, which may be substituted by one or more radicals $R^5$, where one or more $CH_2$ groups in the alkyl and alkoxy groups may be replaced by $-O-$, $-S-$ or $-R^5C=CR^5-$, or a siloxanyl group having 1 to 6 Si atoms, which may be substituted by one or more radicals $R^5$.

It is very particularly preferred for at least one side chain $R^1$, preferably both side chains $R^1$, to be selected from straight-chain alkyl or alkoxy groups having 3 to 20, in particular 4 to 15 C atoms, or branched alkyl or alkoxy groups having 3 to 20, in particular 4 to 15 C atoms, or cyclic alkyl groups having 6 C atoms, or $N(R^{10})_2$ groups, where $R^{10}$ is selected, independently of one another, from alkyl having 1 to 10 C atoms. A branched chain $R^1$ preferably has at least one centre of chirality.

It is especially preferred for both side chains $R^1$ to be alkyl groups having at least 2, preferably 3 to 20, in particular 4 to 15 C atoms, preferably branched, preferably having a centre of chirality.

$R^3$ is preferably on each occurrence, identically or differently, H, F, or an alkyl group having 1 to 10 C atoms, which may be substituted by one or more radicals $R^5$. $R^3$ is particularly preferably on each occurrence, identically or differently, H or F.

$R^4$ is preferably on each occurrence, identically or differently, H, D, F, CN, or an alkyl or alkoxy group having 1 to 10 C atoms, which may be substituted by one or more radicals $R^5$. $R^4$ is particularly preferably on each occurrence, identically or differently, H or F.

$R^5$ is on each occurrence, identically or differently, H, F, CN, or an alkyl or alkoxy group having 1 to 10 C atoms, which may be substituted by one or more radicals $R^6$, or an aryl or heteroaryl group having 5 to 30 aromatic ring atoms, which may in each case be substituted by one or more radicals $R^6$, or a siloxanyl group having 1 to 6 Si atoms, which may be substituted by one or more radicals $R^6$.

The index i is preferably equal to 1, 2 or 3, particularly preferably equal to 1 or 2, very particularly preferably equal to 1.

The compounds of the formula (I) are not polymers. They have not been prepared by means of polymerisation. They thus differ crucially from the dichroic dyes described in the prior art for photo- and electrochemistry, which are generally polymers.

The compounds of the formula (I) preferably have in total 3 to 5 aromatic ring structures. Aromatic ring structure thus denotes a ring, or an annellated ring system, which preferably has 2 to 4 annellated rings. The compound of the formula (I) particularly preferably has 5 ring systems, namely a central TDIM group and 2 aromatic rings connected to one another on each side. The aromatic ring structures are preferably linked to one another via C—C single bonds.

The radicals $R^1$ preferably each have at least 2 C atoms, in particular each have at least one alkyl chain having at least 2 C atoms.

The compounds of the formula (I) particularly preferably have in total 3 to 5 aromatic ring structures, and the radicals $R^1$ each have at least one alkyl chain having at least 2, preferably having 3 to 20 C atoms.

In a preferred embodiment, the compound of the formula (I) is a chiral compound. It is preferably employed as racemate or as a mixture of stereoisomers (d, l or meso). The compound of the formula (I) preferably has one, preferably one or two branched side chains $R^1$ which have a centre of chirality.

In a preferred embodiment, the compound of the formula (I) is asymmetrical in the sense that the two bonded to the central TDIM group are not identical.

Such compounds often have particular electronic properties, in particular particular fluorescence properties.

In a preferred embodiment, the compound of the formula (I) has mesophases at <200° C.

Preferred embodiments of the formula (I) conform to the following formulae (Ia) and (Ib):

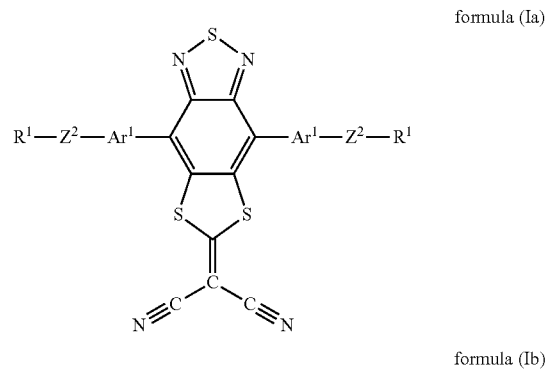

formula (Ia)

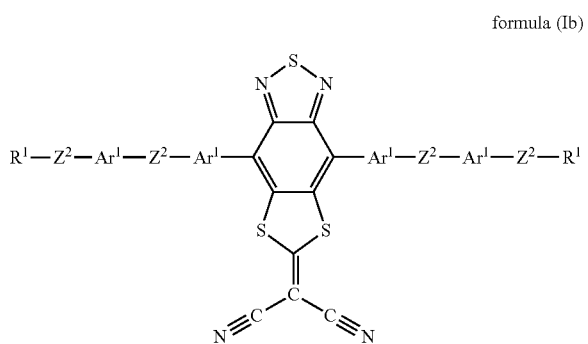

formula (Ib)

where the groups occurring are defined as above.

For formulae (Ia) and (Ib), the above-mentioned preferred embodiments of the groups $Ar^1$, $Z^2$ and $R^1$ preferably apply.

In accordance with the invention and in particular for the formulae (Ia) and (Ib), it is preferred that at least one $Ar^1$ bonded directly to the TDIM structural unit stands for a sulfur-containing heteroaryl group, particularly preferably for thiophene. The group may be substituted by one or more radicals $R^4$. Compounds of this type are distinguished by particularly high light stability.

In a preferred embodiment, all radicals $Z^1$ and $Z^2$ are single bonds. The compound of the formula (I) then has the formula (Ic):

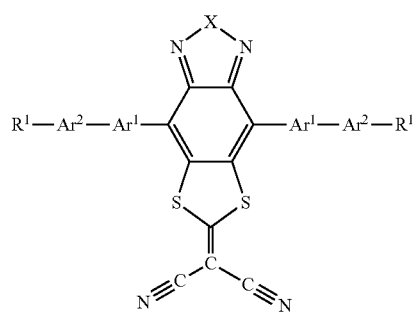

where the groups occurring are defined as above. The formula (Ic) preferably contains the preferred groups $Ar^1$ and $R^1$ indicated above, where $Ar^2$ is selected like $Ar^1$.

Preferred embodiments of the formulae (Ia) and (Ib) conform to the following formulae:

formula (Ia-1)
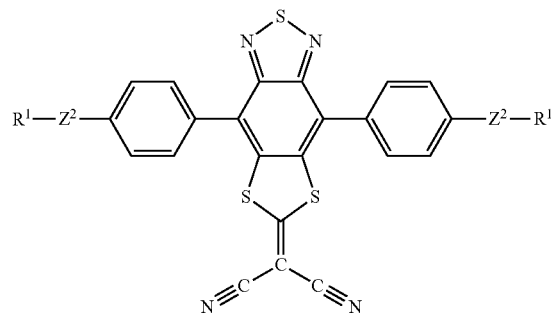
formula (Ia-2)
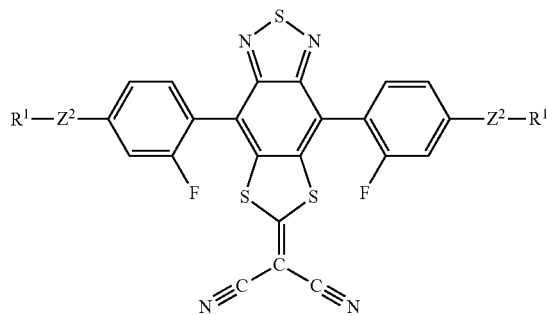
formula (Ia-3)
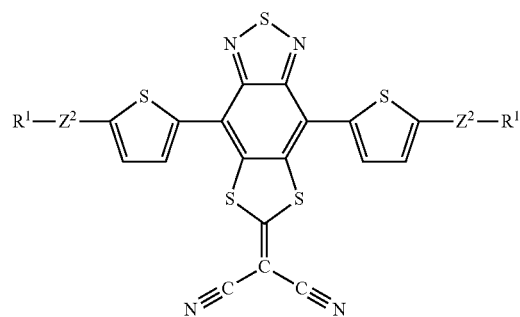
formula (Ia-4)
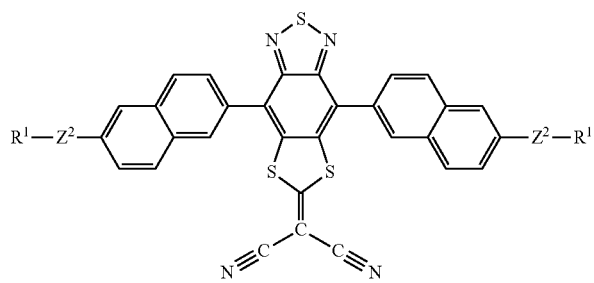
formula (Ib-1)
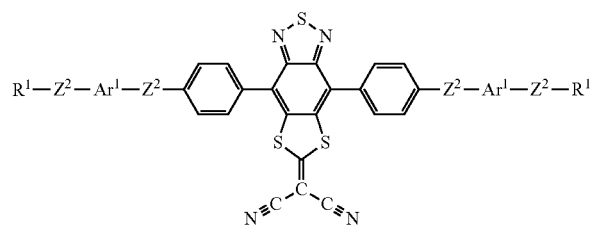
formula (Ib-2)
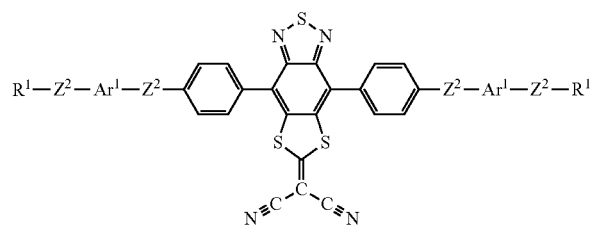
formula (Ib-3)
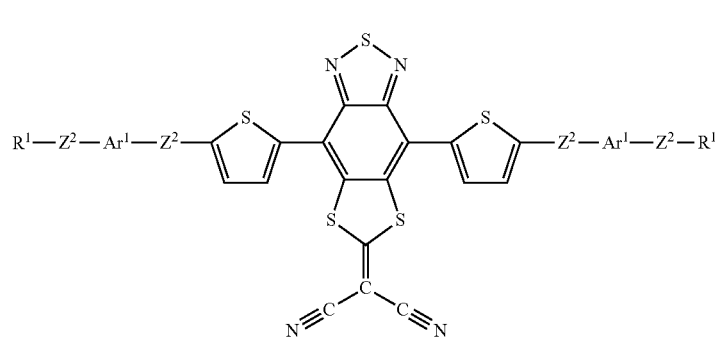
formula (Ib-4)
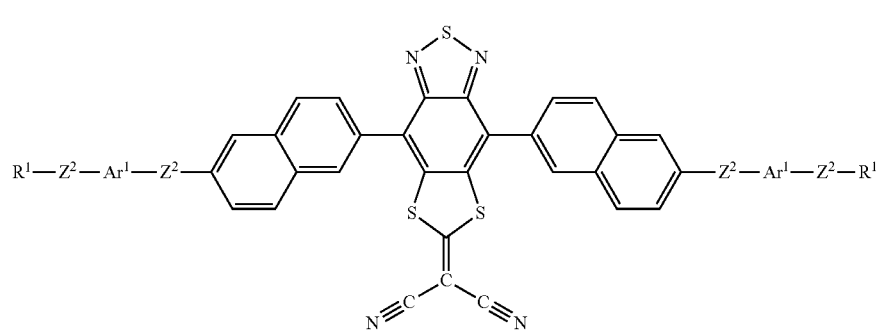

where the groups Ar¹, Z² and R¹ are defined as indicated above.

Particularly preferred compounds of the formula (I) are those of the following formulae (IIa) to (IIc):

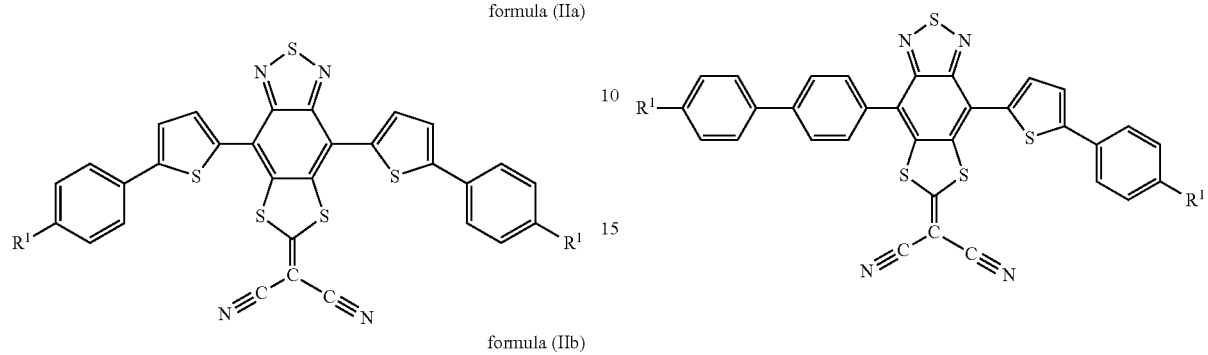

-continued where the radicals R¹ are defined, independently of one another, as indicated above. The benzene and thiophene rings may be fluorinated. Preferably, not more than one fluorine is present per ring.

The present invention furthermore relates to compounds of the formula (I) which conform to the following formulae (III) and (IV):

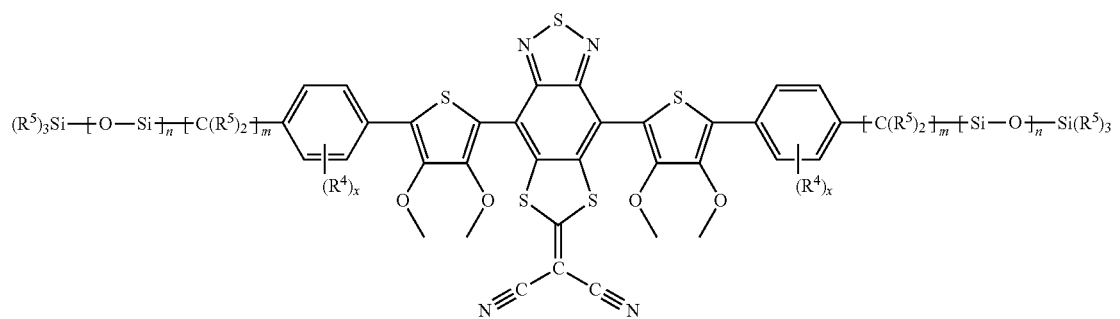

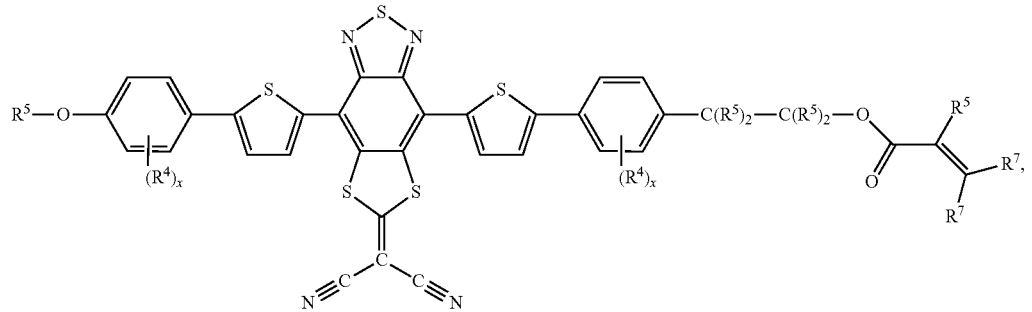

where:
the groups $R^4$ and $R^5$ occurring are defined as above, $R^7$ is defined like $R^5$ above, and k is, identically or differently on each occurrence, 0, 1, 2, 3 or 4;

m is, identically or differently on each occurrence, 0, 1, 2, 3, 4, 5 or 6;

n is, identically or differently on each occurrence, 1, 2, 3, 4 or 5.

In a preferred embodiment, the index k in the formulae (III) and (IV) is, identically or differently, 0 or 1, particularly preferably identically 0.

In a preferred embodiment, the index m in the formulae (III) and (IV) is, identically or differently, 0, 1 or 2, particularly preferably identically 1 or 2.

In a preferred embodiment, the index n in the formulae (III) and (IV) is, identically or differently, 1, 2 or 3, particularly preferably identically 2.

Furthermore preferably, $R^5$ in the formulae (III) and (IV) is hydrogen or an alkyl group having 1 to 5 C atoms, which may be substituted by one or more radicals $R^6$, particularly preferably methyl.

In a preferred embodiment, $R^7$ in the formulae (III) and (IV) is hydrogen or an alkyl group having 1 to 5 C atoms, which may be substituted by one or more radicals $R^6$, particularly preferably hydrogen.

The compounds of the formulae (III) and (IV) have particularly great advantages in relation to the above-mentioned properties of good solubility in the liquid-crystalline medium, good light stability, high fluorescence and/or high anisotropy of the absorption or dichroic behaviour.

Preferred compounds are those of the following formulae V1 to V15, where compounds V1 to V6 are particularly preferred:

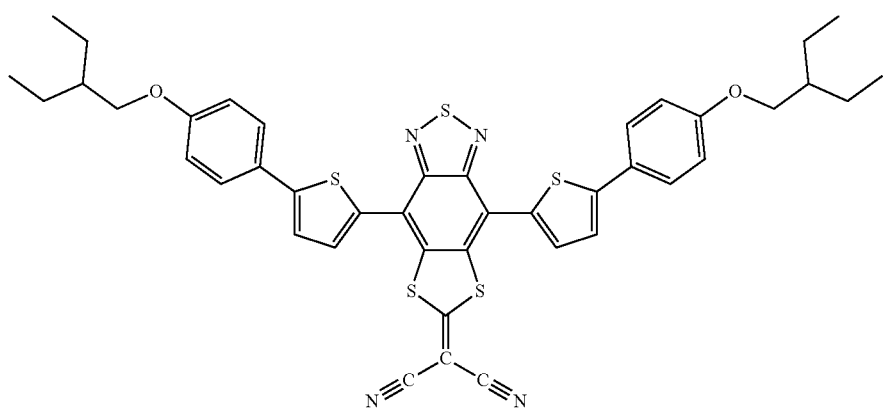

Compound V1

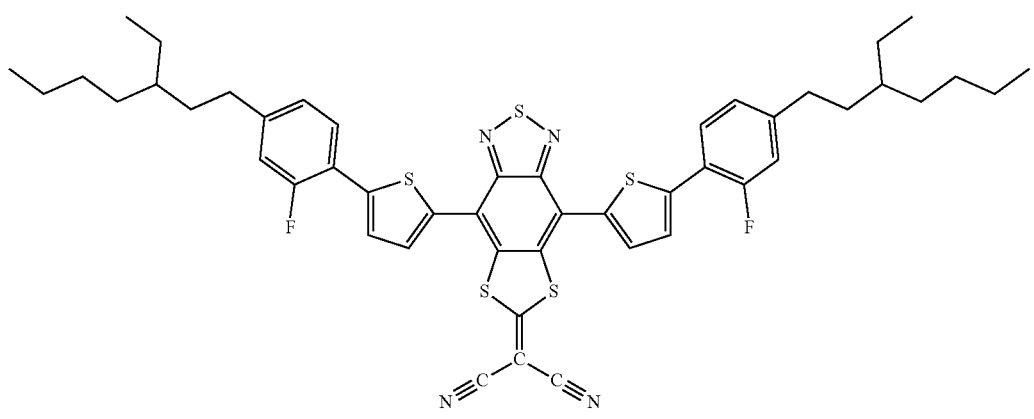

Compound V2

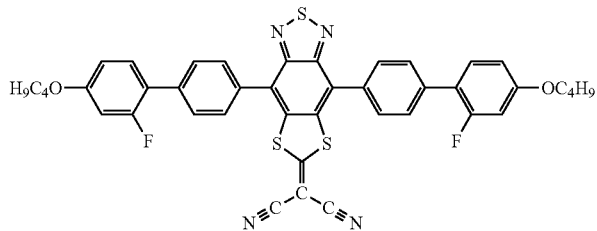

Compound V3

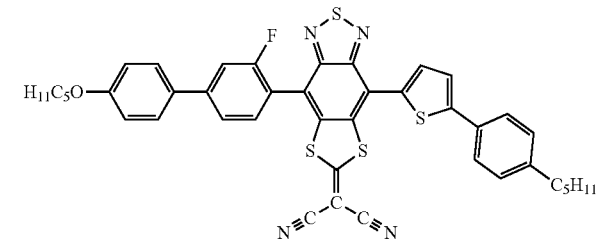

Compound V4

-continued
Compound V5
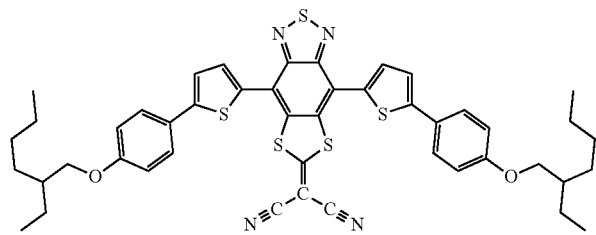
Compound V6
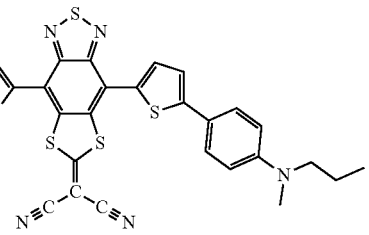
Compound V7
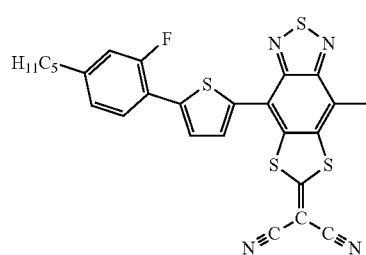
Compound V8
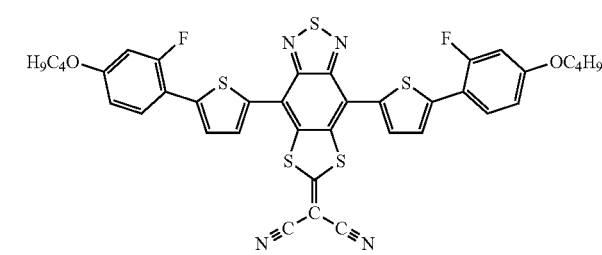
Compound V9
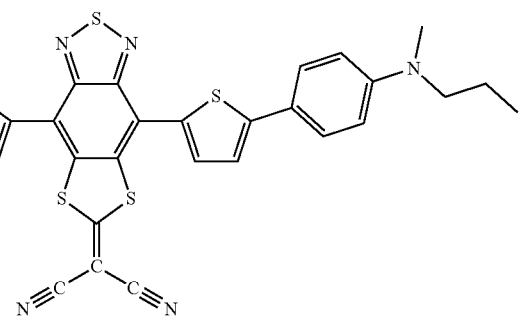
Compound V10
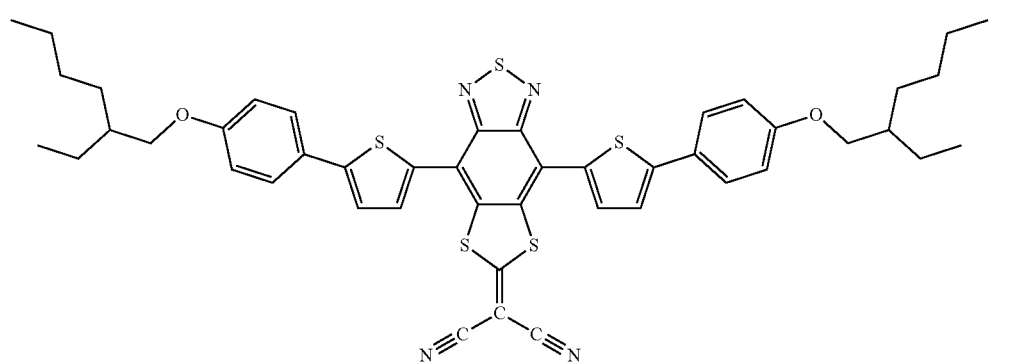
Compound V11
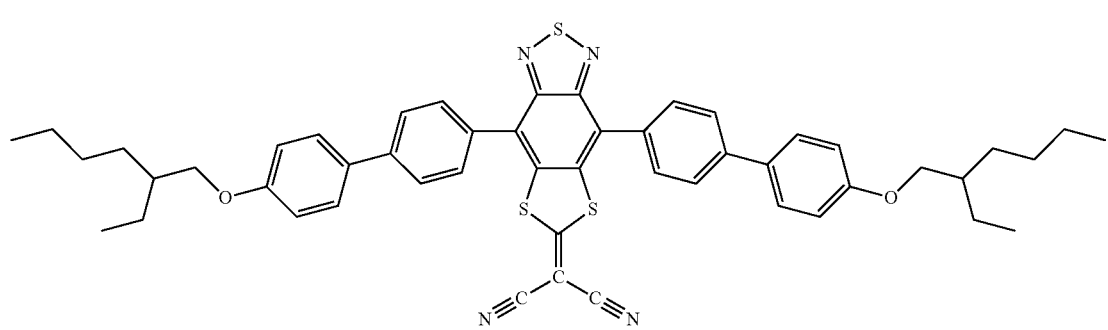

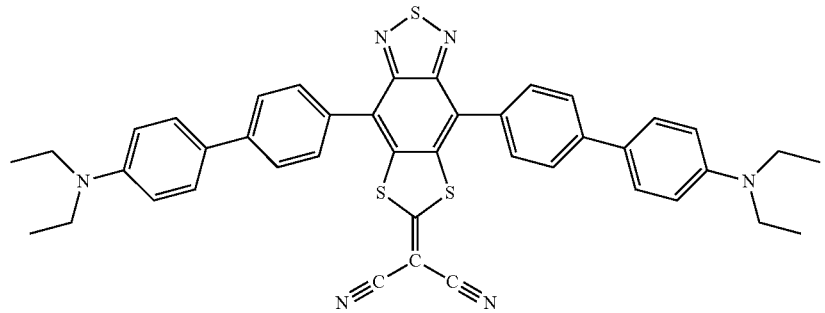

Compound V12

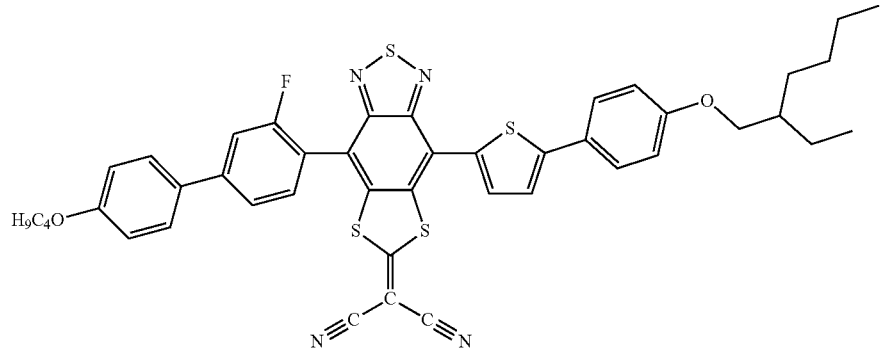

Compound V13

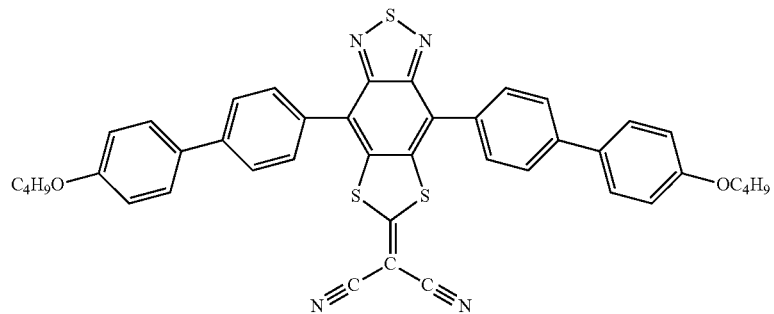

Compound V14

The compounds of the formula (I) described above can be prepared by fundamentally known processes of organic chemistry, in particular by Suzuki coupling between organic bromides and organic boronic acids, or by Stille coupling via the tributylstannyl derivatives. Particularly suitable processes are shown below in general form. For specific processes for the preparation of compounds of the formula (I), reference is furthermore made to the known literature and to the working examples.

In a preferred embodiment, the compounds are prepared starting from dihalodifluorobenzothiadiazole, in particular dibromodifluorobenzothiadiazole.

The following general synthesis schemes 1 to 3 show by way of example how to prepare compounds of the formula (I), in particular compounds of the formulae (IIa), (IIb) and (IIc). The syntheses start from dihalodifluorobenzothiadiazole, in particular dibromodifluorobenzothiadiazole. The preparation of such compounds is described in Zhang et al., 2011, and Li et al., 2014. The couplings are carried out by standard methods via the boronic acid (Suzuki coupling) or tributylstannyl derivatives (Stille coupling). In the schemes, the radical R corresponds to the radical $R^1$ of formula (I), NBS stands for N-bromosuccinimide, NMP stands for N-methyl-2-pyrrolidone.

Scheme 1: Synthesis of compounds of the formula (IIa)
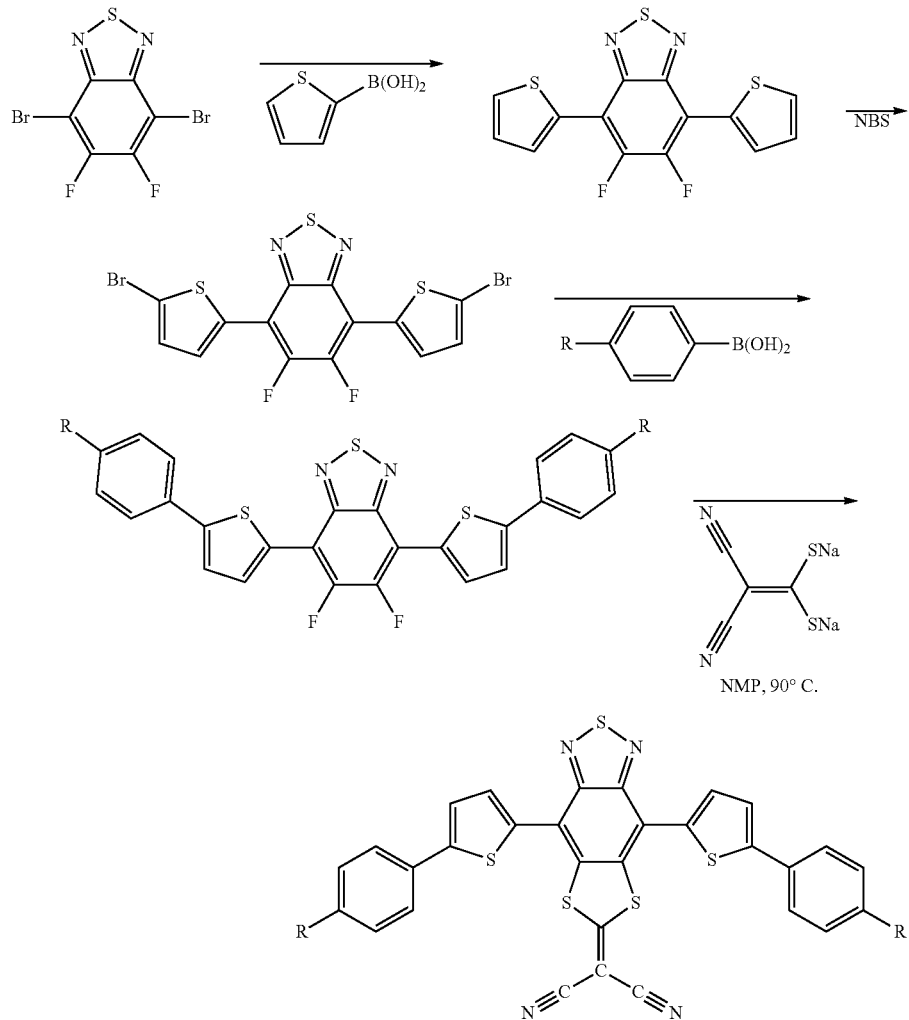
Scheme 2: Synthesis of compounds of the formula (IIb)
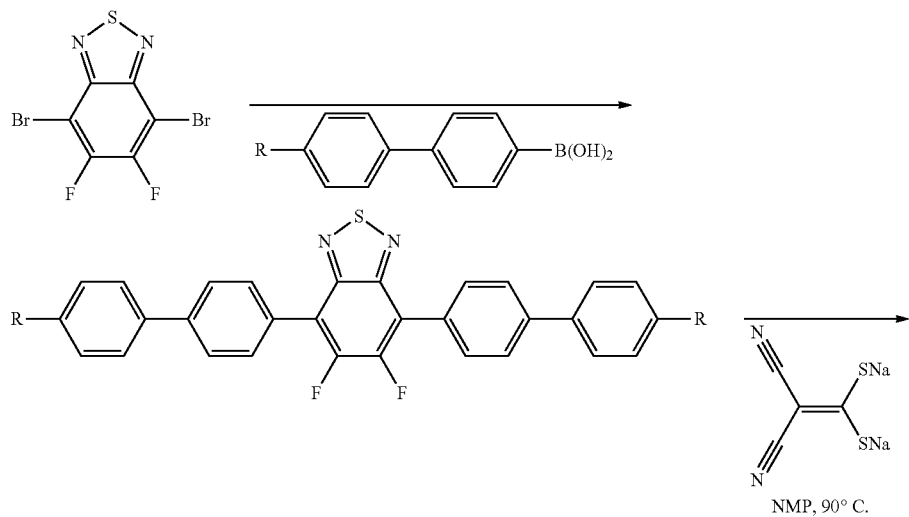

-continued
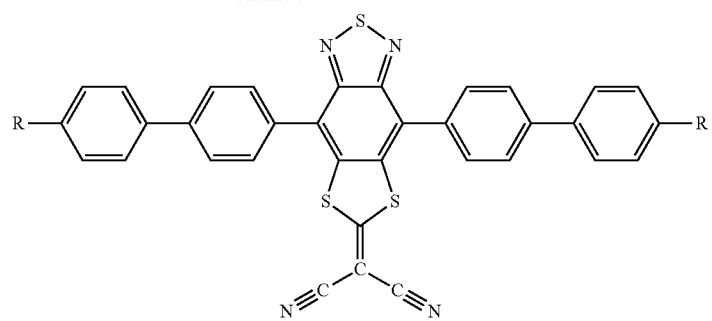
Scheme 3: Synthesis of compounds of the formula (IIc)
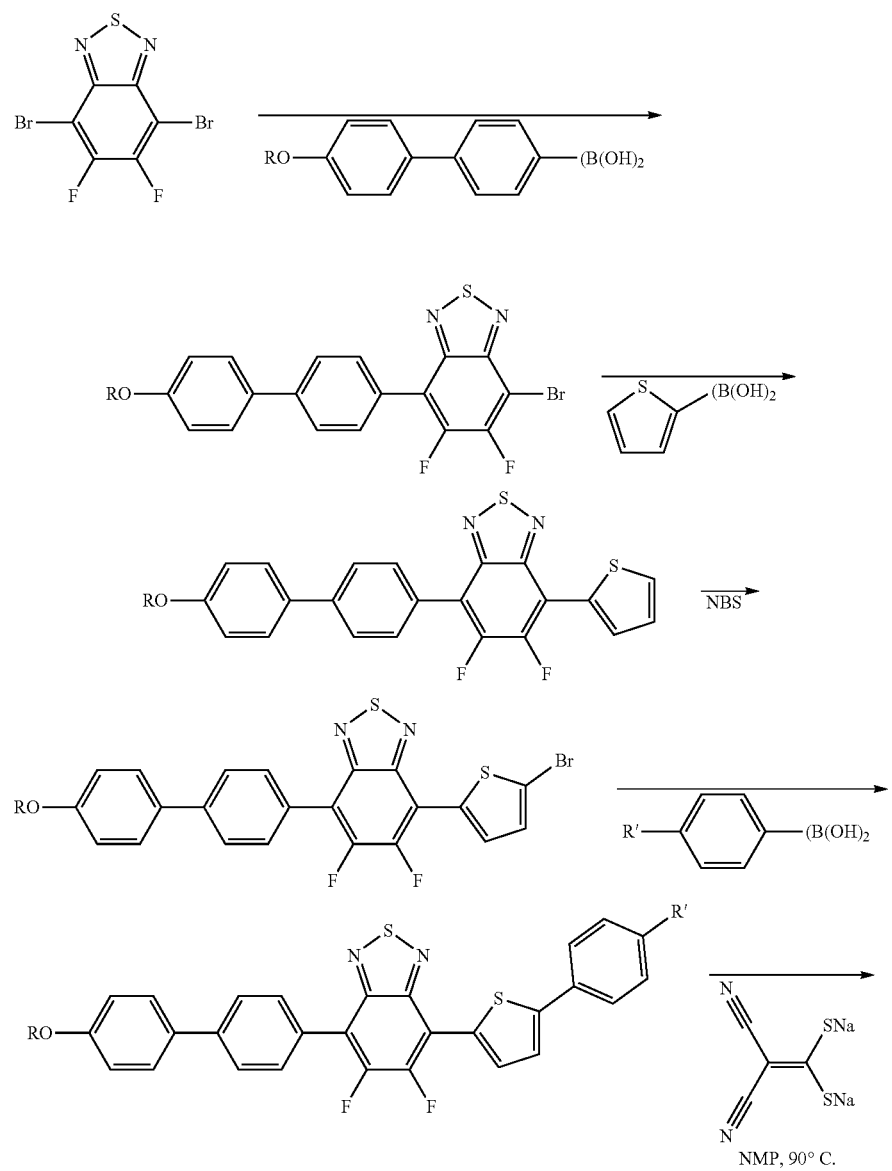

-continued

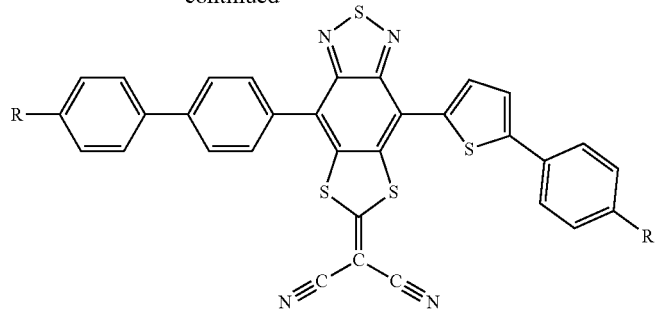

The invention also relates to a device containing at least one of the compounds according to the invention.

The device is selected, in particular, from windows, in particular a switchable window, organic solar cells, in particular bulk heterojunction solar cells, liquid-crystal displays (guest-host LCDs), semiconductors (donor or acceptor), organic electronic components, such as field-effect transistors, diodes or OLEDs. The dyes can also be employed for colouring a polymer matrix, for example in the automobile sector.

The compound of the formula (I) is preferably a dye having positive dichroism, i.e. a dye which has a positive degree of anisotropy R. The degree of anisotropy R is particularly preferably greater than 0.4, very particularly preferably greater than 0.6 and most preferably greater than 0.7. The degree of anisotropy can be determined, for example, as indicated in the working example of EP14002950.5, filed on 25 Aug. 2014.

The absorption preferably reaches a maximum when the polarisation direction of the light is parallel to the direction of the longest elongation of the molecule of the formula (I), and it reaches a minimum when the polarisation direction of the light is perpendicular to the direction of the longest elongation of the molecule of the formula (I).

The compounds of the formula (I) preferably have a small band gap and good absorption above 450 nm. They preferably have an absorption band above 450 nm.

The compound of the formula (I) is furthermore preferably a fluorescent dye. Fluorescence here is taken to mean that a compound is placed in an electronically excited state by absorption of light of a certain wavelength, where the compound subsequently undergoes a transition into the ground state with emission of light. The emitted light preferably has a longer wavelength than the absorbed light. The transition from the excited state into the ground state is furthermore preferably spin-allowed, i.e. takes place without a change in the spin. Furthermore preferably, the lifetime of the excited state of the fluorescent compound is shorter than $10^{-5}$ s, particularly preferably shorter than $10^{-6}$ s, very particularly preferably between $10^{-9}$ and $10^{-7}$ s.

The dichroic compound of the formula (I) is preferably present in the switching layer in a proportion of 0.01 to 10% by weight, particularly preferably 0.05 to 7% by weight and very particularly preferably 0.1 to 7% by weight.

Besides the compound of the formula (I), a liquid-crystalline medium comprising one or more different compounds is preferably present in the switching layer. The liquid-crystalline medium preferably represents the principal component of the mixture of the switching layer of the device. The dichroic compound of the formula (I) is preferably in the form of a solution in the switching layer. It is preferably influenced in its alignment by the alignment of the compounds of the liquid-crystalline medium.

For the purposes of the present application, the term liquid-crystalline medium is taken to mean a material which has liquid-crystalline properties under certain conditions. The material preferably has liquid-crystalline properties at room temperature and in a certain temperature range above and below room temperature. The liquid-crystalline medium may comprise a single compound, or it may comprise a plurality of different compounds.

The liquid-crystalline medium in accordance with the invention typically comprises at least one compound whose molecules have an elongated shape, i.e. are significantly longer in one spatial direction (longitudinal axis) than in the other two spatial directions.

The invention furthermore relates to the use of a mixture comprising a liquid-crystalline medium and at least one compound of a formula (I) in a device for regulating the passage of energy from an outside space into an inside space.

The liquid-crystalline medium of the switching layer preferably has a clearing point, preferably a phase transition from a nematic liquid-crystalline state to an isotropic state, in the temperature range from 70° C. to 170° C., preferably from 90° C. to 160° C., particularly preferably from 95° C. to 150° C. and very particularly preferably from 105° C. to 140° C.

Furthermore, the dielectric anisotropy of the liquid-crystalline medium of the switching layer is preferably greater than 3, particularly preferably greater than 7.

In a further preferred embodiment, the dielectric anisotropy of the liquid-crystalline medium of the switching layer is less than zero, preferably less than −2.

The liquid-crystalline medium of the switching layer furthermore preferably has an optical anisotropy (Δn) of 0.01 to 0.3, particularly preferably of 0.04 to 0.27.

The liquid-crystalline medium of the switching layer furthermore preferably comprises 3 to 20 different liquid-crystalline compounds, preferably 8 to 18, particularly preferably 12 to 16 different liquid-crystalline compounds.

Compounds which can be used as constituents of the liquid-crystalline medium are known to the person skilled in the art and can be selected freely.

It is preferred for the liquid-crystalline medium of the switching layer to comprise at least one compound which contains structural elements based on 1,4-phenylenes and 1,4-cyclohexylenes which are substituted by one or more fluorine atoms or one or more nitrile groups. It is particularly preferred for the liquid-crystalline medium of the switching layer to comprise at least one compound which contains 2, 3 or 4, particularly preferably 3 or 4 structural elements based on 1,4-phenylenes and 1,4-cyclohexylenes.

It is furthermore preferred for the liquid-crystalline medium of the switching layer to comprise one or more chiral dopants. In this case, the molecules of the liquid-crystalline medium are preferably twisted with respect to one another in the switching layer of the device, particularly preferably as known from the TN mode of displays.

Chiral dopants are preferably used in the liquid-crystalline medium of the switching layer in a total concentration of 0.01 to 3% by weight, particularly preferably 0.05 to 1% by weight. In order to obtain high values for the twist, the total concentration of the chiral dopants may also be selected higher than 3% by weight, preferably up to a maximum of 10% by weight.

According to an alternative, likewise preferred embodiment, the liquid-crystalline medium of the switching layer comprises no chiral dopants. In this case, the molecules of the liquid-crystalline medium are preferably not twisted with respect to one another in the switching layer.

The proportions of these compounds and other components present in small amounts are neglected when specifying the proportions of the liquid-crystalline compounds and the dichroic dyes.

The liquid-crystalline medium of the switching layer furthermore preferably comprises one or more stabilisers. The total concentration of the stabilisers is preferably between 0.00001 and 10% by weight, particularly preferably between 0.0001 and 1% by weight of the entire mixture. The proportions of these compounds and other components present in small amounts are neglected when specifying the proportions of the liquid-crystalline compounds and the dichroic dyes.

In addition to one or more compounds of the formula (I), and preferably a liquid-crystalline medium, the device according to the invention preferably also comprises further dichroic dyes having a different structure to formula (I) in the switching layer. It particularly preferably comprises one, two, three or four further dyes, very particularly preferably two or three further dyes and most preferably three further dyes having a different structure to formula (I).

With respect to the property of dichroism, the preferred properties described for the compound of the formula (I) are also preferred for the optional further dichroic dyes.

The absorption spectra of the dichroic dyes of the switching layer preferably complement one another in such a way that the impression of a black colour arises for the eye. The two or more dichroic dyes of the liquid-crystalline medium according to the invention preferably cover a large part of the visible spectrum. The precise way in which a mixture of dyes which appears black or grey to the eye can be prepared is known to the person skilled in the art and is described, for example, in Manfred Richter, Einführung in die Farbmetrik [Introduction to Colorimetry], 2nd Edition, 1981, ISBN 3-11-008209-8, Verlag Walter de Gruyter & Co.

The setting of the colour location of a mixture of dyes is described in the area of colorimetry. To this end, the spectra of the individual dyes are calculated taking into account the Lambert-Beer law to give an overall spectrum and converted into the corresponding colour locations and luminance values under the associated illumination, for example illuminant D65 for daylight, in accordance with the rules of colorimetry. The position of the white point is fixed by the respective illuminant, for example D65, and is quoted in tables (for example reference above). Different colour locations can be set by changing the proportions of the various dyes.

According to a preferred embodiment, the switching layer, in addition to the at least one compound of the formula (I), comprises one or more dichroic dyes which absorb light in the red and NIR region, i.e. at a wavelength of 600 to 2000 nm, preferably in the range from 650 to 1800 nm, particularly preferably in the range from 650 to 1300 nm. In a preferred embodiment, these dichroic dyes are selected from azo compounds, anthraquinones, methine compounds, azomethine compounds, merocyanine compounds, naphthoquinones, tetrazines, perylenes, terrylenes, quaterrylenes, higher rylenes, pyrromethenes, azo dyes, nickel dithiolenes, (metal) phthalocyanines, (metal) naphthalocyanines, (metal) porphyrins, diketopyrrolopyrroles and benzothiadiazoles Of these, particular preference is given to perylenes and terrylenes.

The proportion of all dichroic dyes in the mixture of the switching layer is preferably in total 0.01 to 10% by weight, particularly preferably 0.1 to 7% by weight and very particularly preferably 0.2 to 7% by weight.

The additional dichroic dyes of the switching layer which do not conform to the formula (I) are furthermore preferably selected from the dye classes indicated in B. Bahadur, Liquid Crystals—Applications and Uses, Vol. 3, 1992, World Scientific Publishing, Section 11.2.1, and particularly preferably from the explicit compounds given in the table present therein.

The said dyes which do not conform to the formula (I) belong to the classes of dichroic dyes which are known to the person skilled in the art and have been described many times in the literature. Thus, for example, anthraquinone dyes are described in EP 34832, EP 44893, EP 48583, EP 54217, EP 56492, EP 59036, GB 2065158, GB 2065695, GB 2081736, GB 2082196, GB 2094822, GB 2094825, JP-A 55-123673, DE 3017877, DE 3040102, DE 3115147, DE 3115762, DE 3150803 and DE 3201120, naphthoquinone dyes are described in DE 3126108 and DE 3202761, azo dyes in EP 43904, DE 3123519, WO 82/2054, GB 2079770, JP-A 56-57850, JP-A 56-104984, U.S. Pat. Nos. 4,308,161, 4,308,162, 4,340,973, T. Uchida, C. Shishido, H. Seki and M. Wada: Mol. Cryst. Liq. Cryst. 39, 39-52 (1977), and H. Seki, C. Shishido, S. Yasui and T. Uchida: Jpn. J. Appl. Phys. 21, 191-192 (1982), and perylenes are described in EP 60895, EP 68427 and WO 82/1191. Rylene dyes as described, for example, in EP 2166040, US 2011/0042651, EP 68427, EP 47027, EP 60895, DE 3110960 and EP 698649. Benzothiadiazols are described, for example, in WO 2014/187529, and diketopyrrolopyrroles are described, for example, in WO 2015/090497.

According to a preferred embodiment, the switching layer of the device comprises, besides compounds of the formula (I), exclusively dichroic dyes selected from rylene dyes.

Examples of preferred further dichroic dyes which do not conform to formula (I) and which may be present in the switching layer of the device are depicted in the following table:

TABLE 2
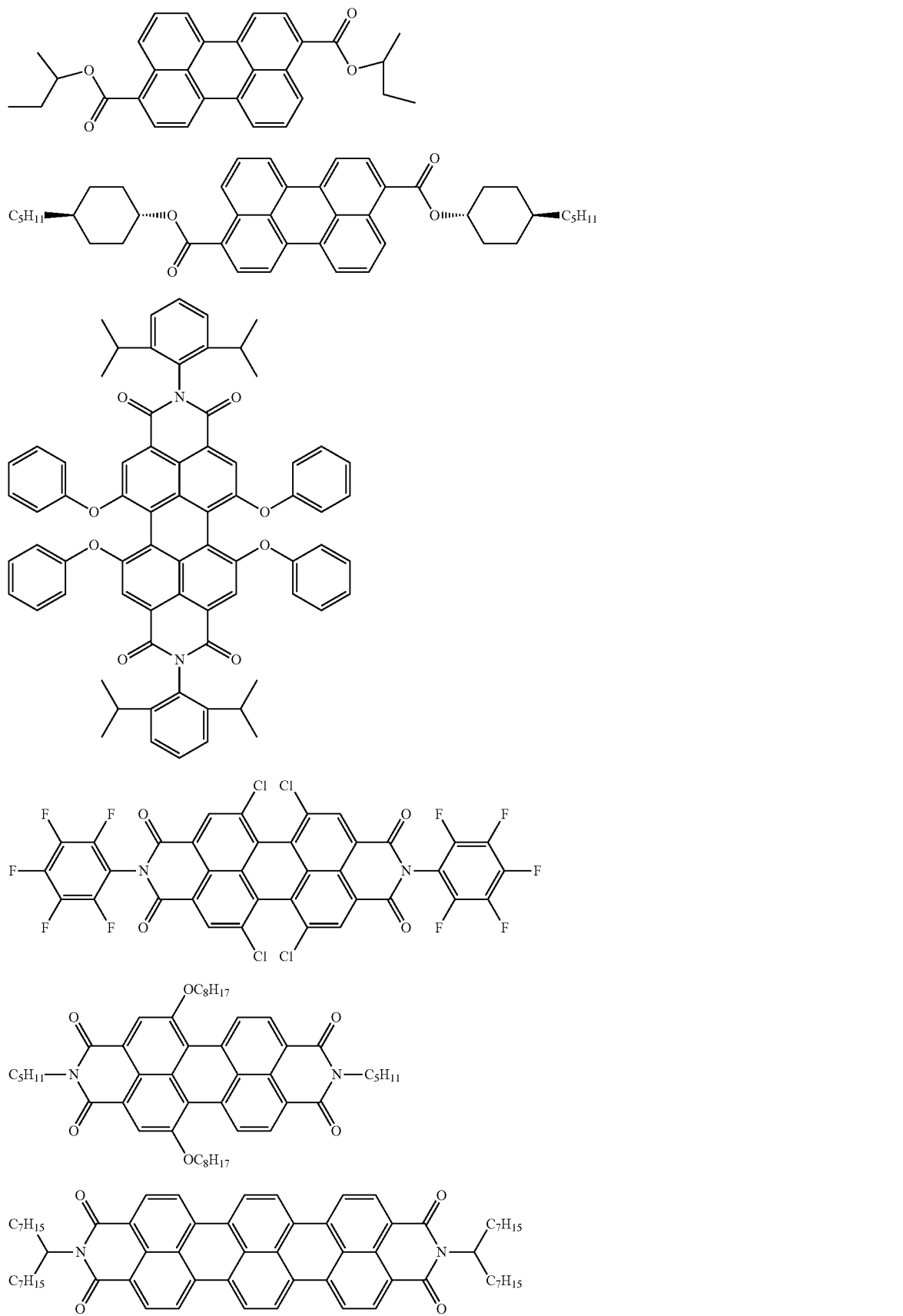

TABLE 2-continued
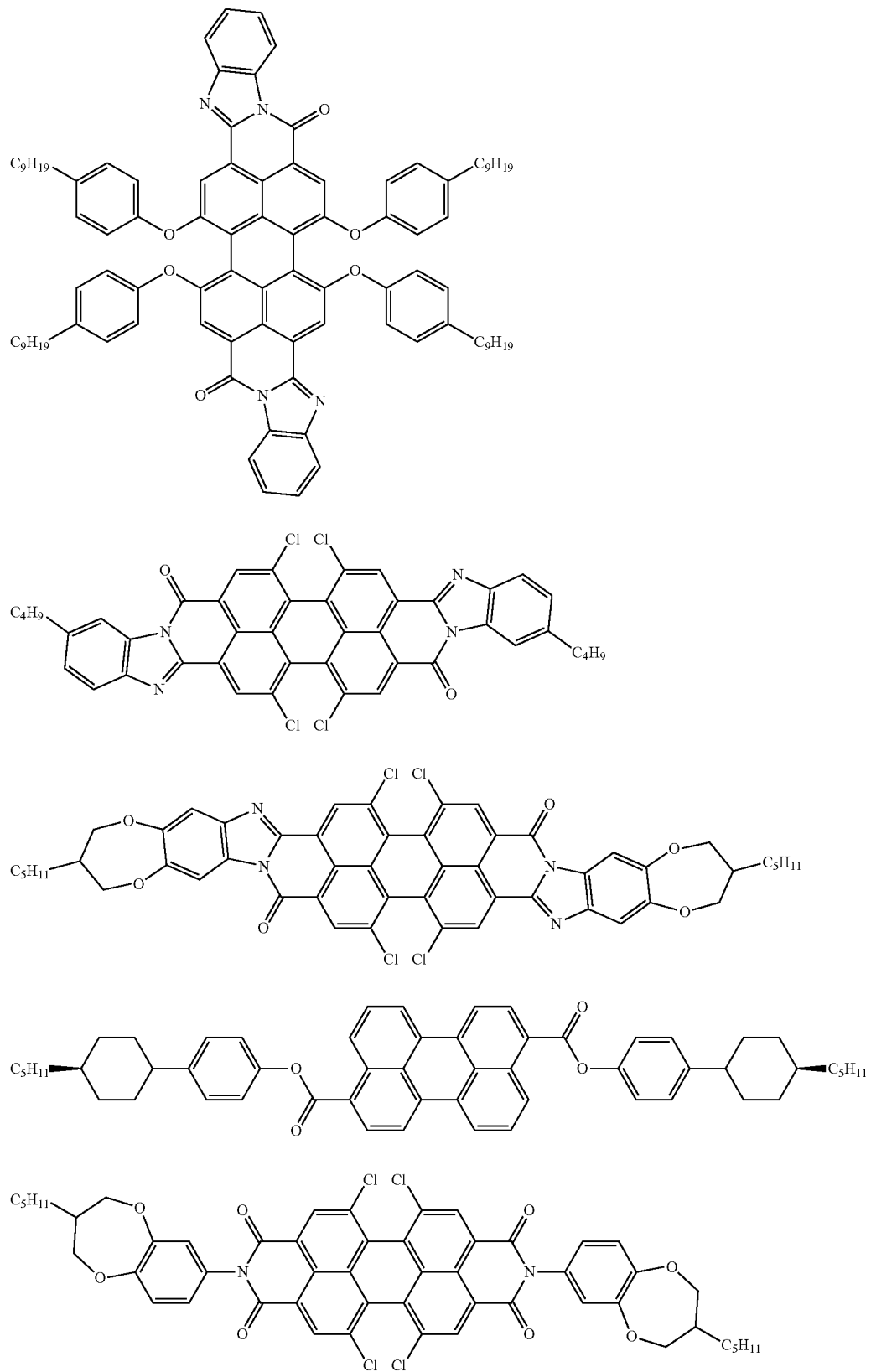

TABLE 2-continued
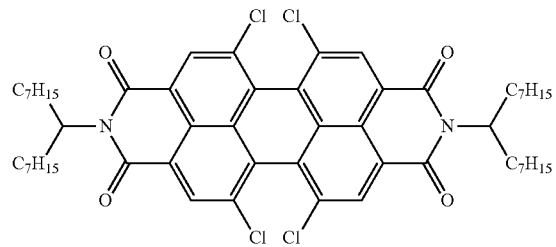
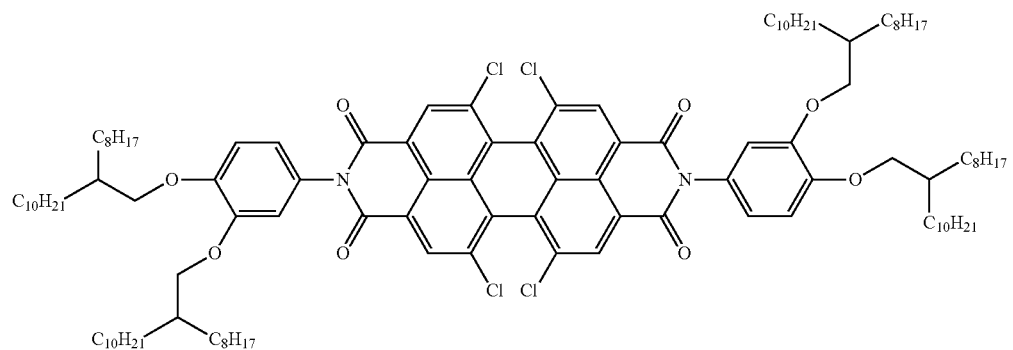
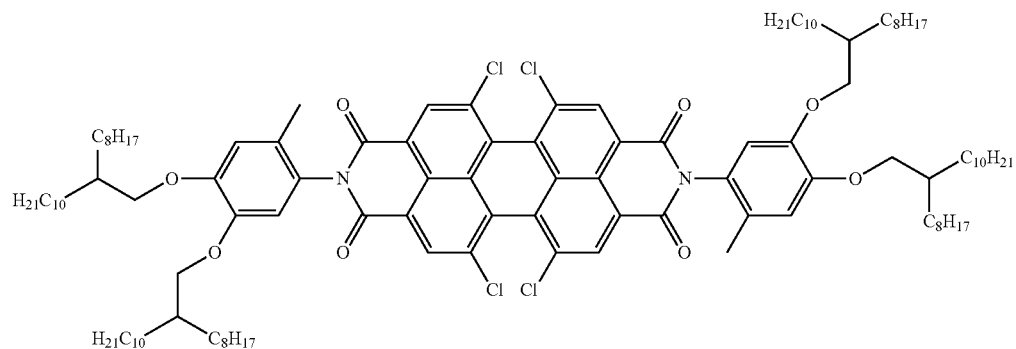
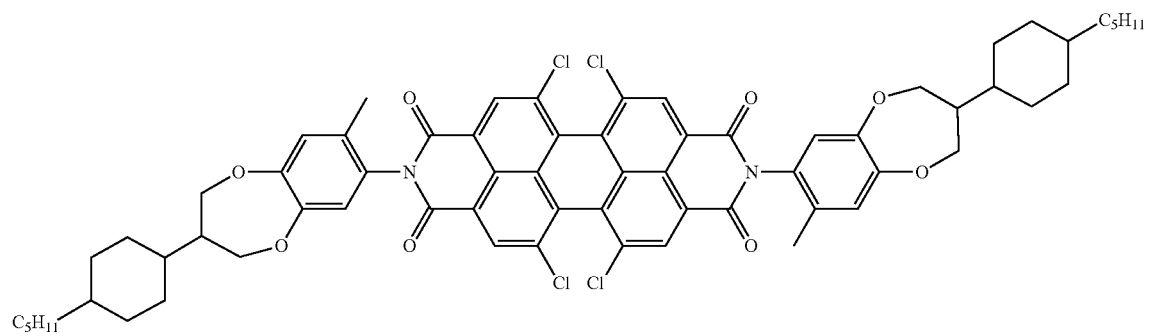
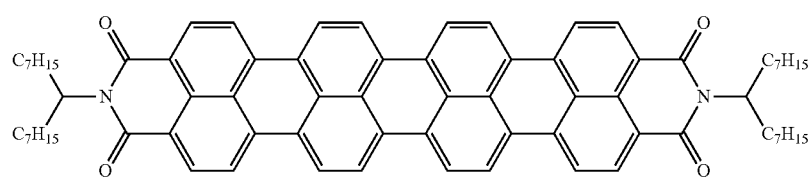

TABLE 2-continued
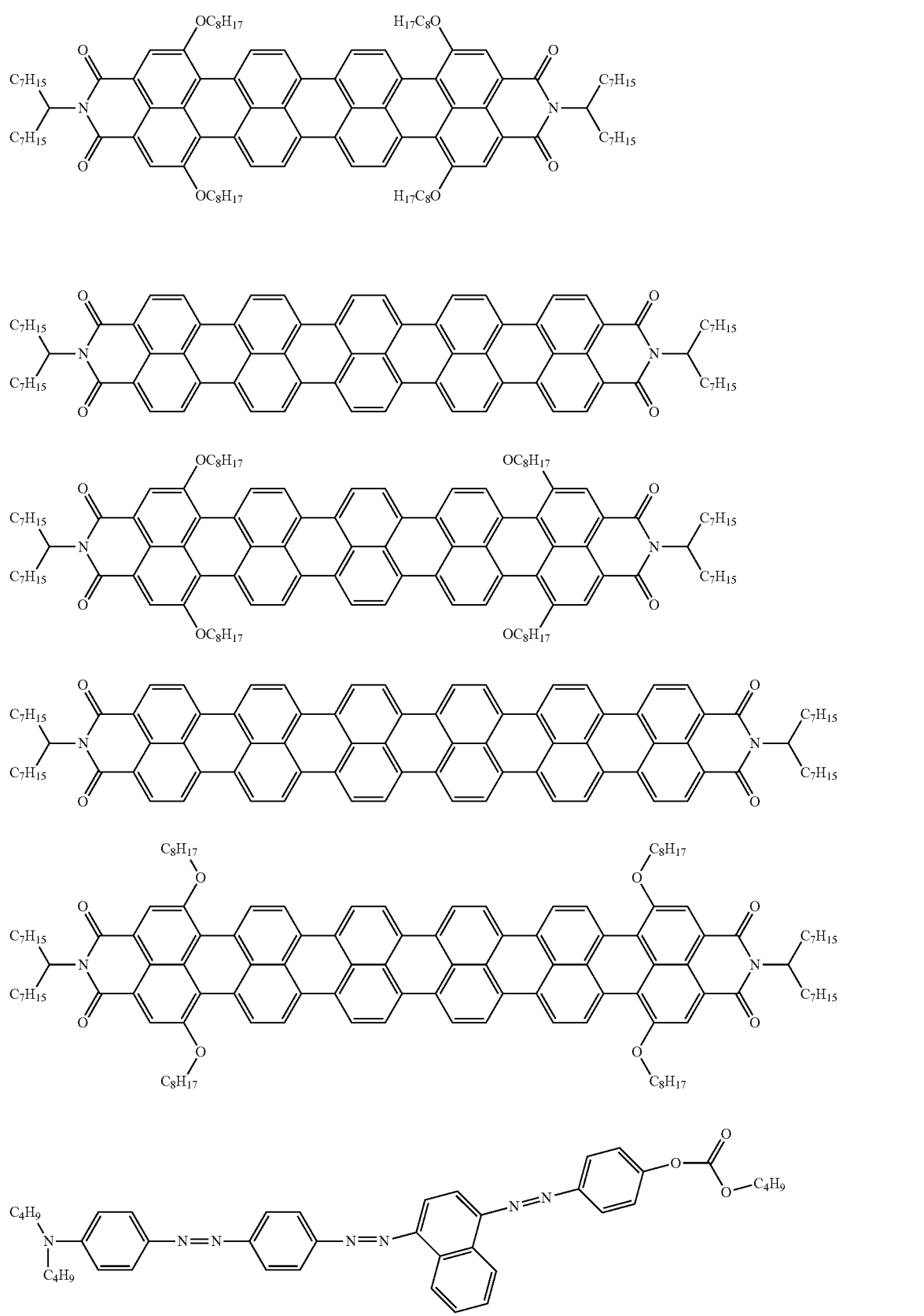

TABLE 2-continued

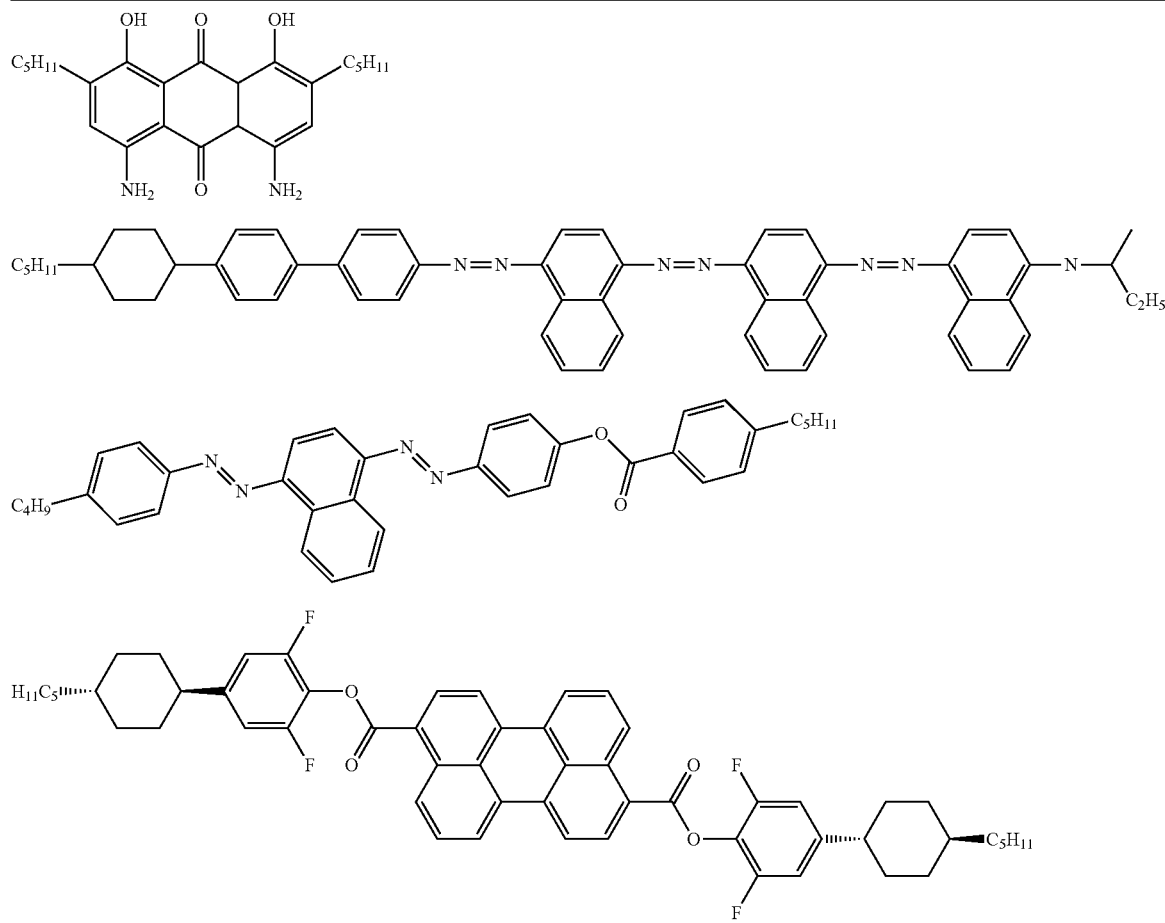

In a preferred embodiment, the switching layer of the device comprises one or more quencher compounds. This is particularly preferred if the device comprises one or more fluorescent dyes in its switching layer.

Quencher compounds are compounds which quench the fluorescence. The quencher compounds can take on the electronic excitation energy of adjacent molecules, such as, for example, fluorescent dyes, in the switching layer and undergo a transition into an electronically excited state in the process. The quenched fluorescent dye is thus converted into the electronic ground state and is thus prevented from emitting fluorescence or undergoing a subsequent reaction. The quencher compound itself returns to the ground state through radiation-free deactivation or by emission of light and is again available for further quenching.

The quencher compound may have various functions in the switching layer of the device. Firstly, the quencher compound may contribute to extending the lifetime of a dye system, by deactivation of electronic excitation energy.

Secondly, the quencher compound eliminates additional colour effects which may be aesthetically undesired, for example coloured emission in the inside space emanating from the fluorescent dyes in the switching layer.

In order to achieve effective quenching, the quencher compound should be adapted to the respective dye system, in particular the dye absorbing at the longest wavelength in a dye combination. The way to do this is known to the person skilled in the art.

Preferred quencher compounds are described, for example, in Table 8.1 on page 279 in Joseph R. Lakowicz, Principles of Fluorescence Spectroscopy, $3^{rd}$ Edition, 2010, ISBN 10: 0-387-31278-1, Verlag Springer Science+Business Media LLC. Further classes of molecule are familiar to the person skilled in the art, for example under the key words dark quencher or black hole quencher. Examples are azo dyes and aminoanthraquinones. The quencher compounds used in the switching layer of the device according to the invention may also be non-fluorescent dyes or dyes which only fluoresce in the NIR.

In a preferred embodiment of the switching layer according to the invention, any quencher compounds present are selected so that fluorescence in the visible part of the spectrum is suppressed.

The device according to the invention is preferably suitable for regulating the passage of energy in the form of light emitted by the sun from the environment into an inside space. The passage of energy to be regulated here takes place from the environment (the outside space) into an inside space.

The inside space here can be any desired space that is substantially sealed off from the environment, for example a building, a vehicle or a container.

The invention therefore furthermore relates to the use of the device for regulating the passage of energy from an outside space into an inside space. However, the device can also be employed for aesthetic room design, for example for light and colour effects. For example, door and wall elements containing the device according to the invention in grey or in colour can be switched to transparent. Furthermore, the device may also comprise white or coloured flat backlighting which is modulated in brightness or yellow flat backlighting which is modulated in colour by means of a blue guest-host display. One or both glass sides of the device may be provided with roughened or structured glass for the coupling-out of light and/or for the generation of light effects.

In a further alternative use, the device is employed for regulating the incidence of light on the eyes, for example in protective goggles, visors or sunglasses, where the device keeps the incidence of light on the eyes low in one switching state and reduces the incidence of light less in another switching state.

The device is preferably arranged in an opening in a relatively large two-dimensional structure, where the two-dimensional structure itself only allows slight passage of energy, or none at all, and where the opening has relatively high energy transmissivity. The two-dimensional structure is preferably a wall or another boundary of an inside space to the outside. Furthermore, the two-dimensional structure preferably covers an area of at least equal size, particularly preferably an area at least twice as large as the opening in it in which the device is disposed.

The device is preferably characterised in that it has an area of at least $0.05$ $m^2$, preferably at least $0.1$ $m^2$, particularly preferably at least $0.5$ $m^2$ and very particularly preferably at least $0.8$ $m^2$.

The device is preferably accommodated in an opening having relatively high energy transmissivity, as described above, in a building, a container, a vehicle or another substantially closed space. The device can generally be used for any desired inside spaces, particularly if they have only limited exchange of air with the environment and have light-transmitting boundary surfaces through which input of energy from the outside in the form of light energy can take place. The use of the device for inside spaces which are subjected to strong insolation through light-transmitting areas, for example through window areas, is particularly relevant.

The device is switchable. Switching here is taken to mean a change in the passage of energy through the device. The device is preferably electrically switchable, as described, for example, in WO 2009/141295 and in WO 2014/090373.

However, it may also be thermally switchable, as described, for example, in WO 2010/118422. In this case, the switching preferably takes place through a transition from a nematic state to an isotropic state through a change in the temperature of the switching layer comprising the compound of the formula (I) and a liquid-crystalline medium. In the nematic state, the molecules of the liquid-crystalline medium are in ordered form and thus so is the compound of the formula (I), for example aligned parallel to the surface of the device through the action of an alignment layer. In the isotropic state, the molecules are in unordered form, and thus so is the compound of the formula (I). The difference between ordered and unordered presence of the dichroic compound of the formula (I) causes a difference in the light transmissivity of the switching layer of the device, in accordance with the principle that dichroic compounds have a higher or lower absorption coefficient depending on the alignment in relation to the plane of vibration of the light.

If the device is electrically switchable, it preferably comprises two or more electrodes, which are installed on both sides of the switching layer. The electrodes preferably consist of ITO or a thin, preferably transparent metal and/or metal-oxide layer, for example silver or FTO (fluorine-doped tin oxide) or an alternative material known to the person skilled in the art for this use. The electrodes are preferably provided with electrical connections.

The voltage is preferably provided by a battery, a rechargeable battery or an external power supply.

The switching operation in the case of electrical switching takes place through an alignment of the molecules of the liquid-crystalline medium by the application of voltage.

In a preferred embodiment, the device is converted from a state having high absorption, i.e. low light transmissivity, which is present without voltage, into a state having lower absorption, i.e. higher light transmissivity. The liquid-crystalline medium of the switching layer is preferably nematic in both states. The voltage-free state is preferably characterised in that the molecules of the liquid-crystalline medium, and thus the molecules of the compound of the formula (I), are aligned parallel to the plane of the switching layer. This is preferably achieved by a correspondingly selected alignment layer. The state under voltage is preferably characterised in that the molecules of the liquid-crystalline medium, and thus the molecules of the compound of the formula (I), are perpendicular to the plane of the switching layer.

In an alternative embodiment to the embodiment mentioned above, the device is converted from a state having low absorption, i.e. high light transmissivity, which is present without voltage, into a state having higher absorption, i.e. lower light transmissivity. The liquid-crystalline medium of the switching layer is preferably nematic in both states. The voltage-free state is preferably characterised in that the molecules of the liquid-crystalline medium of the switching layer, and thus the molecules of the compound of the formula (I), are aligned perpendicular to the plane of the switching layer. This is preferably achieved by a correspondingly selected alignment layer. The state under voltage is preferably characterised in that the molecules of the liquid-crystalline medium of the switching layer, and thus the molecules of the compound of the formula (I), are parallel to the plane of the switching layer.

According to a preferred embodiment of the invention, the device can be operated without an external power supply by providing the energy required by means of a solar cell or another device for conversion of light and/or heat energy into electrical energy which is connected to the device. The provision of the energy by means of the solar cell can take place directly or indirectly, i.e. via a battery or rechargeable battery or other unit for the storage of energy connected in-between. The solar cell is preferably mounted on the outside of the device or is an internal component of the device, as disclosed, for example, in WO 2009/141295. Particular preference is given here to solar cells which are particularly efficient in the case of diffuse light, and transparent solar cells.

The device preferably has the following layer sequence, where further layers may additionally be present. The layers indicated below are preferably directly adjacent to one another in the device:
  substrate layer, preferably comprising glass or polymer
  electrically conductive transparent layer, preferably comprising ITO
  alignment layer
  switching layer comprising one or more compounds of the formula (I)

alignment layer electrically conductive transparent layer, preferably comprising ITO substrate layer, preferably comprising glass or polymer The preferred embodiments of the individual layers are described below.

The device preferably comprises one or more, particularly preferably two, alignment layers. The alignment layers are preferably directly adjacent to the two sides of the switching layer comprising the compound of the formula (I).

The alignment layers used in the device can be any desired layers known to the person skilled in the art for this purpose. Preference is given to polyimide layers, particularly preferably layers comprising rubbed polyimide.

Polyimide rubbed in a certain manner known to the person skilled in the art results in alignment of the molecules of the liquid-crystalline medium in the rubbing direction if the molecules are parallel to the alignment layer (planar alignment). It is preferred here for the molecules of the liquid-crystalline medium not to be completely planar on the alignment layer, but instead to have a slight pretilt angle. In order to achieve vertical alignment of the compounds of the liquid-crystalline medium to the surface of the alignment layer (homeotropic alignment), polyimide treated in a certain manner is preferably employed as material for the alignment layer (polyimide for very high pretilt angles). Furthermore, polymers obtained by an exposure process to polarised light can be used as alignment layer in order to achieve alignment of the compounds of the liquid-crystalline medium in accordance with an alignment axis (photoalignment).

The switching layer in the device is furthermore preferably arranged between two substrate layers or enclosed thereby. The substrate layers can consist, for example, of glass or a polymer, preferably a light-transmitting polymer.

The device is preferably characterised in that it does not comprise a polymer-based polariser, particularly preferably does not comprise a polariser in the solid material phase and very particularly preferably comprises no polariser at all.

However, in accordance with an alternative embodiment, the device may also comprise one or more polarisers. The polarisers in this case are preferably linear polarisers.

If precisely one polariser is present, its absorption direction is preferably perpendicular to the orientation axis of the compounds of the liquid-crystalline medium of the device on the side of the switching layer on which the polariser is located.

In the device, both absorptive and also reflective polarisers can be employed. Preference is given to the use of polarisers which are in the form of thin optical films. Examples of reflective polarisers which can be used in the device are DRPF (diffusive reflective polariser film, 3M), DBEF (dual brightness enhanced film, 3M), DBR (layered-polymer distributed Bragg reflectors, as described in U.S. Pat. Nos. 7,038,745 and 6,099,758) and APF films (advanced polariser film, 3M, cf. Technical Digest SID 2006, 45.1, US 2011/0043732 and U.S. Pat. No. 7,023,602). It is furthermore possible to employ polarisers based on wire grids (WGPs, wire-grid polarisers) which reflect infrared light. Examples of absorptive polarisers which can be employed in the devices are the Itos XP38 polariser film and the Nitto Denko GU1220DUN polariser film. An example of a circular polariser which can be used in accordance with the invention is the APNCP37-035-STD polariser (American Polarizers). A further example is the CP42 polariser (ITOS).

The device furthermore preferably comprises an optical waveguide system which transports the light to a solar cell or another device for the conversion of light and/or heat energy into electrical energy, preferably as described in WO 2009/141295. The optical waveguide system collects and concentrates light hitting the device. It preferably collects and concentrates light emitted by fluorescent dichroic dyes in the switching layer. The optical waveguide system is in contact with a device for the conversion of light energy into electrical energy, preferably a solar cell, so that the collected light hits the latter in concentrated form. In a preferred embodiment of the invention, the device for the conversion of light energy into electrical energy is mounted at the edge of the device, integrated into the latter and electrically connected to means for the electrical switching of the device.

In a preferred embodiment, the device is a constituent of a window, particularly preferably a window comprising at least one glass surface, very particularly preferably a window which comprises multipane insulating glass.

Window here is taken to mean, in particular, a structure in a building which comprises a frame and at least one glass pane surrounded by this frame. It preferably comprises a heat-insulating frame and two or more glass panes (multi-pane insulating glass).

According to a preferred embodiment, the device is applied directly to a glass surface of a window, particularly preferably in the interspace between two glass panes of multipane insulating glass.

The invention furthermore relates to a window comprising a device according to the invention, preferably having the preferred features indicated above.

FIGURE

Brief Description of Drawing

FIG. 1 shows a UV-VIS spectrum of the compound V2 prepared in accordance with Working Example 2, with absorption peaks at 227, 332, 404, 471 and 487 nanometers. The absorption (OD) is shown as a function of the wavelength (nm).

WORKING EXAMPLES

The examples show the preparation of dichroic fluorescent dyes based on 2-(2,5,7-trithia-1,3-diaza-s-indacen-6-ylidene)malononitrile (TDIM). They are intended to illustrate the present invention and should not be interpreted as restrictive.

Example 1a: Preparation of Compound V1

Compound 3 is prepared from compound 1 in accordance with the synthetic route shown in Scheme 4:

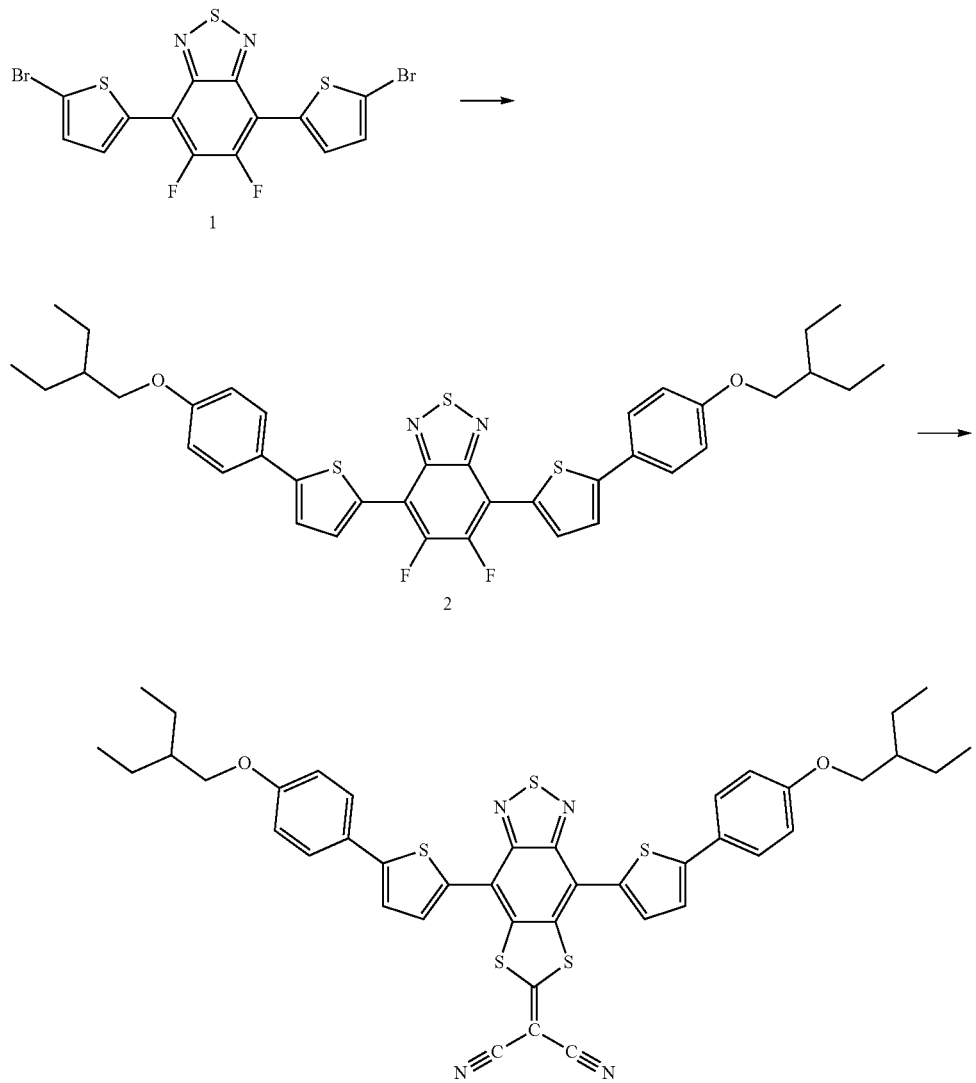

Reaction scheme 4

Preparation of Compound 2

A mixture of 1 (Schroeder et al., 2012; Li et al., 2014) (1.50 g, 3.04 mmol), (2-ethylbutoxy)benzeneboronic acid (1.62 g, 7.3 mmol), tris(dibenzylideneacetone)dipalladium (0) (32 mg, 0.035 mmol), tris(o-tolyl)phosphine (42 mg, 0.138 mmol), toluene (52 ml) and 2 M aqueous $Na_2CO_3$ solution (30 ml) is heated under reflux under an argon atmosphere for 18 h. The mixture is subjected to conventional aqueous work-up. The crude product obtained from the organic extracts is filtered through a silica-gel frit (toluene/n-heptane 1:1) and subsequently crystallised three times from toluene. Yield of compound 2: (1.3 g, 62%) as red crystals, HPLC purity 99.5%.

Preparation of Compound 3

A mixture of 2 (1.00 g, 1.45 mmol) and dimercaptomethylenemalononitrile disodium salt (Hatchard, 1964) (350 mg, 1.88 mmol) and NMP (50 ml) is stirred at 90° C. under an argon atmosphere for 18 h. The mixture is poured into water (300 ml) and allowed to crystallise out for 18 h. The solid which has precipitated out is filtered off with suction and filtered through a silica-gel frit (toluene/n-heptane 1:1). The residue is recrystallised from hot toluene/n-heptane 5:3. Yield of compound 3: (370 mg, 32%) as red crystals, HPLC purity 99.7%. HR-MS ($C_{42}H_{39}O_2N_4S_5$): 791.16664.

Example 1b: Preparation of Compound V2

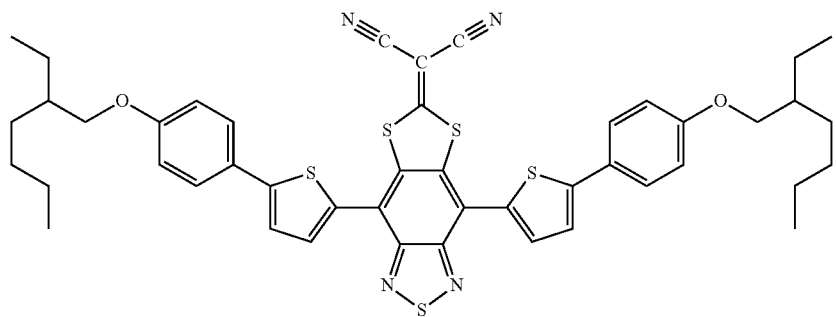 [SMILES: CCCCC(CC)COc1ccc(-c2ccc(-c3c4c(c(-c5ccc(-c6ccc(OCC(CC)CCCC)cc6)s5)c5nsnc35)SC(=C(C#N)C#N)S4)s2)cc1]

Compound V2 is prepared by an analogous route to Example 1a, by coupling a 2-ethylheptyloxy-substituted phenylboronic acid instead of the 2-ethylbutoxyphenylboronic acid indicated in Example 1a.

Example 2: Preparation of Compound V3

Compound 5 is prepared from compound 1 in accordance with the synthetic route shown in Scheme 5:

Reaction scheme 5

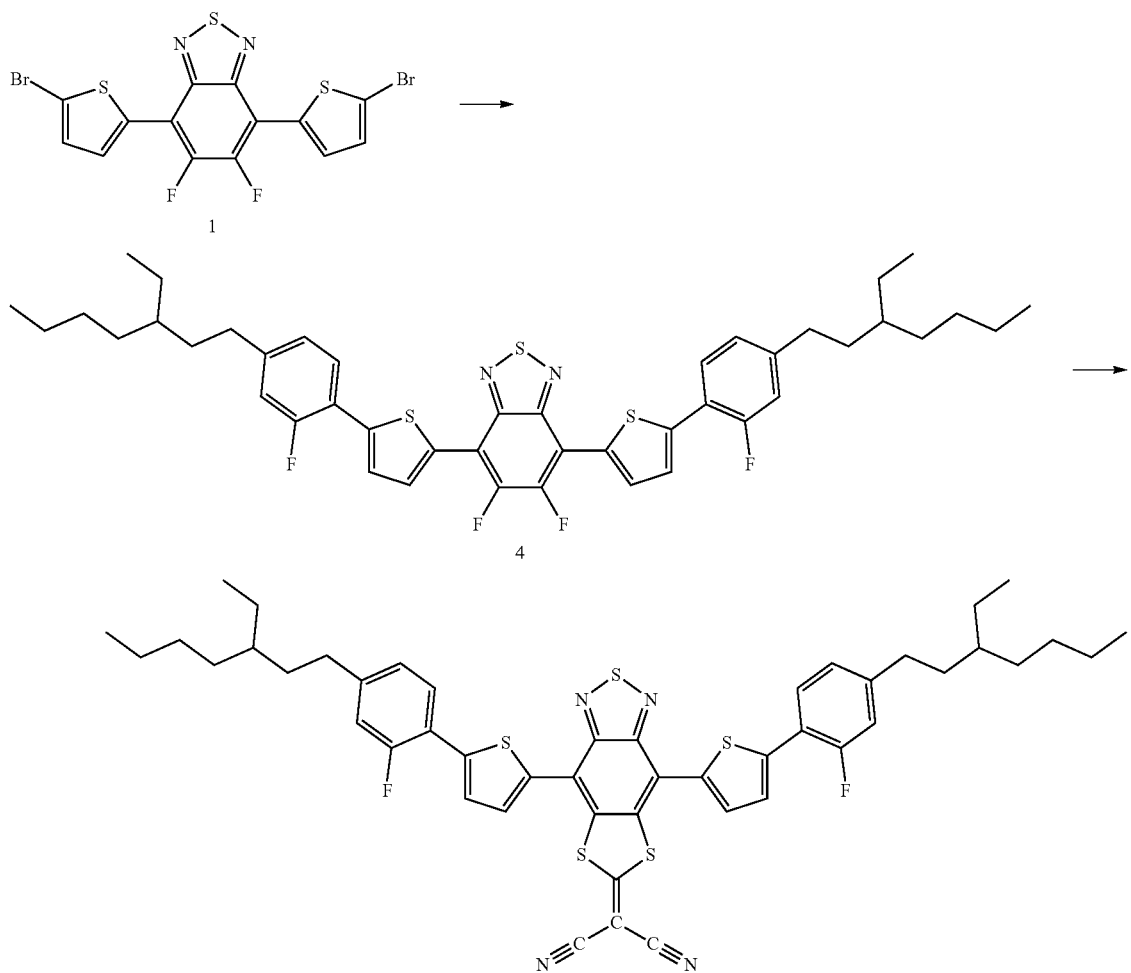

Preparation of Compound 4

A mixture of compound 1 (Schroeder et al., 2012; Li et al., 2014) (8.00 g, 16.19 mmol), 4-(2-ethylheptyl)-2-fluorobenzeneboronic acid (8.80 g, 33.06 mmol), tris(dibenzylideneacetone)dipalladium(0) (171 mg, 0.187 mmol), tris(o-tolyl)phosphine (224 mg, 0.736 mmol), toluene (280 ml) and 2 M aqueous $Na_2CO_3$ solution (65 ml) is heated under reflux under an argon atmosphere for 18 h. The mixture is subjected to conventional aqueous work-up. The crude product obtained from the organic extracts is filtered through a silica-gel frit (toluene/n-heptane 1:4) and subsequently crystallised twice from n-heptane/toluene 1:1. Yield of compound 4: (8.2 g, 66%) as red crystals, HPLC purity 99.3%.

Preparation of Compound 5

A mixture of 4 (1.94 g, 2.5 mmol) and dimercaptomethylenemalononitrile disodium salt (Hatchard, 1964) (930 mg, 5.00 mmol) and NMP (25 ml) is stirred at RT under an argon atmosphere for 24 h. The mixture is poured into water (200 ml) and allowed to crystallise out for 1 h. The solid which has precipitated out is recrystallised from toluene (30 ml) and subsequently filtered through a silica-gel frit (toluene). The residue is recrystallised again from toluene (20 ml). Yield of compound 5: (1.1 g, 50%) as red crystals, HPLC purity 99.4%. HR-MS ($C_{48}H_{49}N_4F_2S_5$): 879.25234. FIG. 1 shows a UV-VIS spectrum of compound 5 (1.3 mg in 100 ml of tetrahydrofuran) with absorption peaks at 227, 332, 404, 471 and 487 nanometers.

Example 3: Measurement of the UV-VIS Absorption Spectra of Compounds V1 and V3

Absorption spectra of the two compounds mentioned above in THF (compound V1, 1.3 mg in 100 ml of tetrahydrofuran, see FIG. 1), or in dichloromethane (compound V3) are recorded.

The spectra have the following peaks:

| Compound | Absorption peaks at [nm] |
|---|---|
| V1 | 330; 345; 400; 520 |
| V3 | 227; 332; 404; 471; 487 |

Example 4: Use of Liquid-Crystalline Media Comprising the Dyes According to the Invention in Devices for Regulating the Passage of Light In order to produce the devices, the liquid-crystal mixture comprising one of the dyes according to the invention is introduced into the interspace of the following layer arrangement (single cell):
substrate layer
ITO layer
polyimide alignment layer
interspace held open using spacers
polyimide alignment layer
ITO layer
substrate layer;
or introduced into the interspaces of the following layer arrangement (double cell):
substrate layer
ITO layer
polyimide alignment layer
interspace held open using spacers
polyimide alignment layer
ITO layer
substrate layer
substrate layer
ITO layer
polyimide alignment layer
interspace held open using spacers
polyimide alignment layer
ITO layer
substrate layer,
i.e. comprising two single cells arranged one behind the other, where the alignment layers of the second single cell have a rubbing direction rotated by 90° relative to the alignment layers of the first single cell (crossed single cells).

The liquid-crystal layer in this arrangement is aligned in a planar manner with antiparallel pretilt angle. This alignment is achieved by two polyimide layers rubbed antiparallel to one another. The thickness of the liquid-crystalline layer is defined by spacers and is usually 25 μm.

Values for the degree of light transmission $\tau_v$ for both the dark and bright switching states of the device are determined and are shown below. The bright switching state is achieved by application of a voltage, while the dark switching state is present without voltage. Furthermore, the colour location of the device (in CIE coordinates) in the dark and bright states is determined.

The measurement is carried out with the device comprising the liquid-crystalline medium with dyes in the measurement beam and a device of the same construction correspondingly without the dyes in the reference beam. Reflection and absorption losses of the cell are thereby eliminated.

The value $\tau_v$ and the CIE coordinates (x,y) are defined as follows:
$\tau_v$=degree of light transmission, determined in accordance with DIN EN410

The colour location (for white, grey, black) of the basic standard illuminant D65 here is at x=0.3127 and y=0.3290 (Manfred Richter, Einführung in die Farbmetrik [Introduction to Colorimetry], second edition 1991, ISBN 3-11-008209-8). The colour locations (x,y) indicated all relate to the standard illuminant D65 and the 2° standard observer in accordance with CIE 1931.

The following mixture serves as host mixture (M1):

| Composition of host mixture M1 | | |
|---|---|---|
| Clearing point | 114.5° C. | |
| Delta-n | 0.1342 | |
| $n_e$ | 1.6293 | |
| $n_o$ | 1.4951 | |
| | Compound | % by weight |
| Composition | CPG-3-F | |
| | CPG-5-F | 5 |
| | CPU-3-F | 5 |
| | CPU-5-F | 15 |
| | CP-3-N | 15 |
| | CP-5-N | 16 |
| | CCGU-3-F | 16 |
| | CGPC-3-3 | 7 |
| | CGPC-5-3 | 4 |
| | CGPC-5-5 | 4 |
| | CCZPC-3-3 | 4 |
| | CCZPC-3-4 | 3 |
| | CCZPC-3-5 | 3 |

These are the structures of the other compounds used below:

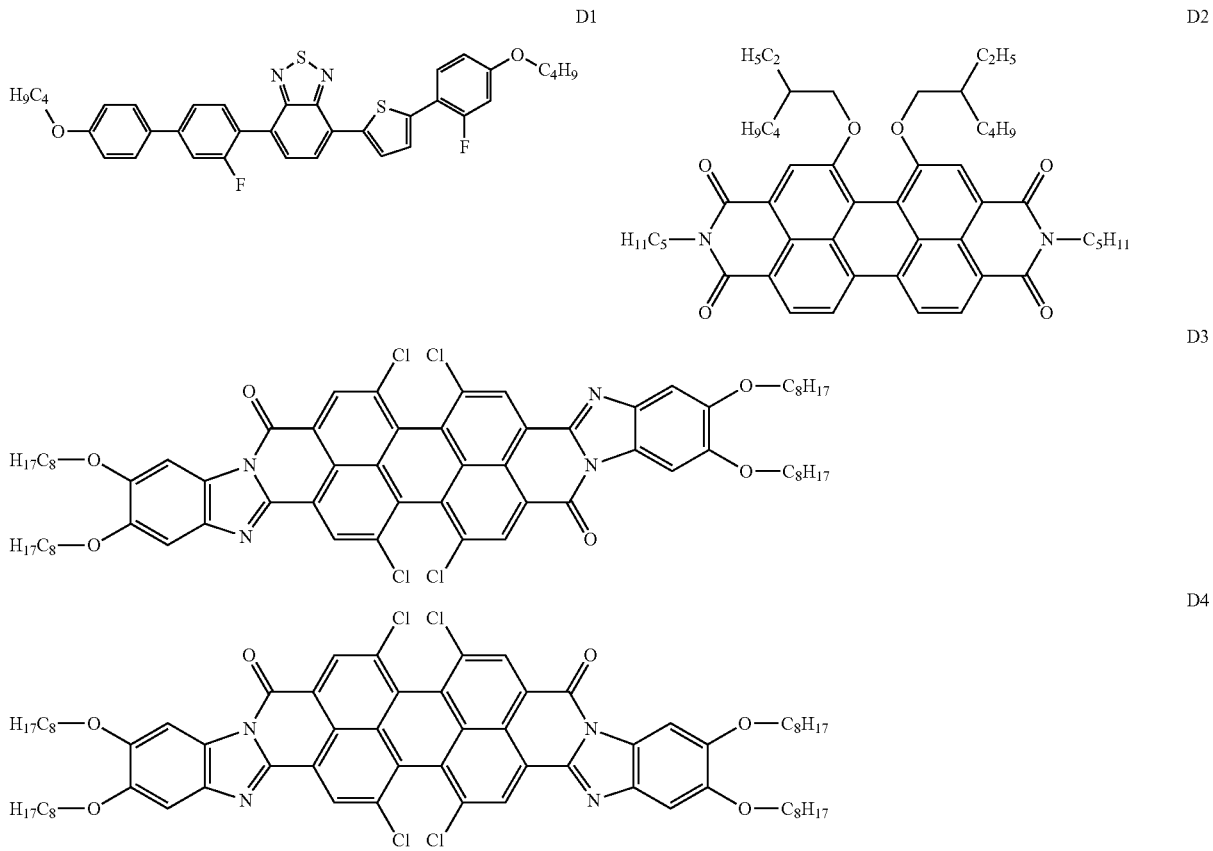

Example 4a

The following liquid-crystalline mixture is used:

| Constituent | Proportion [%] |
|---|---|
| M1 | 99.029 |
| D1 | 0.188 |
| V1 | 0.118 |
| D2 | 0.061 |
| D3 | 0.604 |

Measurement values obtained for the device (double cell, 25 μm in each case):
dark state: x=0.312; y=0.329; $\tau_v$=15%
bright state: x=0.334; y=0.358; $\tau_v$=70.6%

Example 4b

| Constituent | Proportion [%] |
|---|---|
| M1 | 98.035 |
| D1 | 0.221 |
| V1 | 0.243 |
| D2 | 0.158 |
| D3 | 0.680 |
| D4 | 0.663 |

Measurement values obtained for the device (single cell, 25 μm):
dark state: x=0.313; y=0.329; $\tau_v$=38%
bright state: x=0.322; y=0.344; $\tau_v$=72%

Example 4c

| Constituent | Proportion [%] |
|---|---|
| M1 | 99.029 |
| D1 | 0.153 |
| V1 | 0.20 |
| V2 | 0.255 |
| D2 | 0.199 |
| D3 | 1.111 |
| D4 | 1.156 |

Measurement values obtained for the device (single cell, 25 μm):
dark state: x=0.313; y=0.329; $\tau_v$=30%
bright state: x=0.322; y=0.3⁴6; $\tau_v$=60%

The examples show that the device can be switched from a dark state having significantly lower light transmission to a bright state having significantly increased light transmission by application of a voltage.

The invention claimed is:

1. Compound of the formula (I):

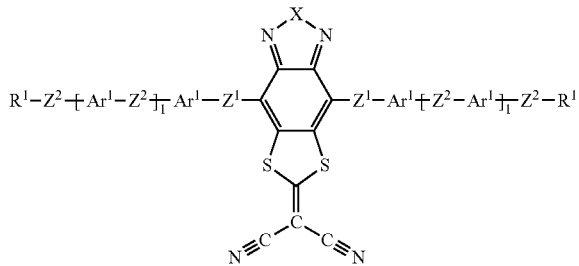

formula (I)

where:

X is equal to S or Se;

$Z^1$ is, independently of one another, a single bond, —$CR^3$=$CR^3$— or —C≡C—; or two, three, four or five groups combined with one another, selected from the groups —$CR^3$=$CR^3$— and —C≡C—;

$Z^2$ is, independently of one another, a single bond, O, S, $C(R^3)_2$, —$CR^3$=$CR^3$— or —C≡C—; or two, three, four or five groups combined with one another, selected from the groups O, S, $C(R^3)_2$, —$CR^3$=$CR^3$— and —C≡C—;

$Ar^1$ is, independently of one another, an aryl or heteroaryl group having 5 to 30 aromatic ring atoms, which may be substituted by one or more radicals $R^4$;

$R^1$ is, independently of one another, H, D, F, CN, $N(R^5)_2$, or an alkyl, alkoxy or thioalkoxy group having 1 to 20 C atoms, which may be substituted by one or more radicals $R^5$, where one or more $CH_2$ groups in the alkyl, alkoxy or thioalkoxy groups may be replaced by —$R^5C$=$CR^5$—, —C≡C—, C=O, C=S, —C(=O)O—, —OC(=O)—, $Si(R^5)_2$, $NR^5$, —O— or —S—;

$R^3$, $R^4$ are, independently of one another, H, D, F, Cl, CN, or an alkyl, alkoxy or thioalkoxy group having 1 to 10 C atoms, which may be substituted by one or more radicals $R^5$, where one or more $CH_2$ groups in the alkyl, alkoxy or thioalkoxy groups may be replaced by —$R^5C$=$CR^5$—, —C≡C—, C=O, C=S, —C(=O)O—, —OC(=O)—, $Si(R^5)_2$, $NR^5$, —O— or —S—;

$R^5$ is, independently of one another, H, D, F, Cl, CN, $N(R^6)_2$, an alkyl, alkoxy or thioalkoxy group having 1 to 10 C atoms or an alkenyl or alkynyl group having 2 to 20 C atoms, where the above-mentioned groups may each be substituted by one or more radicals $R^6$ and where one or more $CH_2$ groups in the above-mentioned groups may be replaced by —$R^6C$=$CR^6$—, —C≡C—, C=O, C=S, —C(=O)O—, —O(C=O)—, $Si(R^6)_2$, $NR^6$, —O— or —S—, or an aryl or heteroaryl group having 5 to 30 aromatic ring atoms, which may in each case be substituted by one or more radicals $R^6$;

$R^6$ is, independently of one another, H, F or an aliphatic organic radical having 1 to 20 C atoms, in which one or more H atoms may be replaced by F, or an aryl or heteroaryl group having 5 to 20 C atoms, in which one or more H atoms may be replaced by F; and i is, independently of one another, equal to 0, 1, 2, 3, 4 or 5.

2. Compound according to claim 1, characterised in that X is equal to S and/or in that $Z^1$ is a single bond.

3. Compound according to claim 1, characterised in that $Z^2$ stands, independently of one another, for a single bond, —$C(R^3)_2C(R^3)_2$—, —$CR^3$=$CR^3$, —C≡C—, —$OC(R^3)_2$— or —$C(R^3)_2O$—.

4. Compound according to claim 1, characterised in that $Z^1$ and $Z^2$ stand for a single bond.

5. Compound according to claim 1, characterised in that $Ar^1$ represents, independently of one another, an aryl group having 6 to 15 C atoms or a heteroaryl group having 5 to 15 C atoms, which may be substituted by one or more radicals $R^4$.

6. Compound according to claim 1, characterised in that $Ar^1$ is selected on each occurrence from benzene, fluorene, naphthalene, pyridine, pyrimidine, pyrazine, triazine, thiophene, thiophene with condensed-on 1,4-dioxane ring, benzothiophene, dibenzothiophene, benzodithiophene, cyclopentadithiophene, thienothiophene, indenothiophene, dithienopyrrole, silolodithiophene, selenophene, benzoselenophene, dibenzoselenophene, furan, benzofuran, dibenzofuran and quinoline, each of which is optionally substituted by radicals $R^4$.

7. Compound according to claim 1, characterised in that at least one $Ar^1$ is selected from a sulfur-containing heteroaryl group, which may be substituted by one or more radicals $R^4$.

8. Compound according to claim 1, characterised in that $R^1$ is selected, independently of one another, from H, F, or a straight-chain alkyl or alkoxy group having 3 to 20 C atoms, which may be substituted by one or more radicals $R^5$, or a branched alkyl or alkoxy group having 3 to 20 C atoms, which may be substituted by one or more radicals $R^5$, or a cyclic alkyl group having 6 C atoms, which may be substituted by one or more radicals $R^5$, where one or more $CH_2$ groups in the alkyl and alkoxy groups may be replaced by —O—, —S— or —$R^5C$=$CR^5$—, or a siloxanyl group having 1 to 6 Si atoms, which may be substituted by one or more radicals $R^5$.

9. Compound according to claim 1, characterised in that $R^1$ is, independently of one another, a branched alkyl group having 4 to 15 C atoms.

10. Compound according to claim 1, characterised in that the index i is equal to 1 or 2.

11. Compound according to claim 1, characterised in that the degree of anisotropy R of the compound of the formula (I) is greater than 0.4.

12. A device for regulating the passage of energy from an outside space into an inside space which is a window or switchable window where the device contains a switching layer, where the switching layer comprises one or more compounds of the formula (I).

13. A device according to claim 12, characterised in that, besides the compound of the formula (I), a liquid-crystalline medium comprising one or more different compounds is present in the switching layer.

14. A device according to claim 12, characterised in that it is electrically switchable.

15. A device according to claim 12, characterised in that it is connected to a solar cell or another device for conversion of light and/or heat energy into electrical energy.

* * * * *